(12) United States Patent
Lee

(10) Patent No.: US 10,974,234 B2
(45) Date of Patent: Apr. 13, 2021

(54) SYNTHESIS OF METAL COMPLEXES AND USES THEREOF

(71) Applicant: Novomer, Inc., Boston, MA (US)

(72) Inventor: Han Lee, Waltham, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 16/054,904

(22) Filed: Aug. 3, 2018

(65) Prior Publication Data

US 2019/0030520 A1    Jan. 31, 2019

Related U.S. Application Data

(63) Continuation of application No. 15/329,027, filed as application No. PCT/US2015/042124 on Jul. 24, 2015, now abandoned.

(60) Provisional application No. 62/028,993, filed on Jul. 25, 2014.

(51) Int. Cl.
| C07D 487/22 | (2006.01) |
| B01J 31/18 | (2006.01) |
| B01J 31/22 | (2006.01) |
| C07F 5/06 | (2006.01) |

(52) U.S. Cl.
CPC ......... *B01J 31/183* (2013.01); *B01J 31/1815* (2013.01); *B01J 31/2243* (2013.01); *C07D 487/22* (2013.01); *C07F 5/069* (2013.01); *B01J 2231/321* (2013.01); *B01J 2531/025* (2013.01); *B01J 2531/0205* (2013.01); *B01J 2531/0252* (2013.01); *B01J 2531/31* (2013.01); *B01J 2531/845* (2013.01)

(58) Field of Classification Search
CPC .................................................. C07D 487/22
See application file for complete search history.

(56) References Cited

U.S. PATENT DOCUMENTS

| 2,245,404 A | 6/1941 | Kise et al. |
| 2,302,321 A | 11/1942 | Hopff et al. |
| 2,469,704 A | 5/1949 | Stone |
| 2,526,554 A | 10/1950 | Gresham et al. |
| 3,002,017 A | 9/1961 | Wearsch et al. |
| 3,006,942 A | 10/1961 | Nobis et al. |
| 3,326,938 A | 6/1967 | Wagner |
| 3,751,435 A | 8/1973 | Van Der Ven et al. |
| 3,800,006 A | 3/1974 | Katayama et al. |
| 3,960,912 A | 6/1976 | Mueller et al. |
| 4,026,967 A | 5/1977 | Flexman, Jr. et al. |
| 4,081,253 A | 3/1978 | Marion |
| 4,590,293 A | 5/1986 | Pascoe |
| 4,873,378 A | 10/1989 | Murphy et al. |
| 5,096,470 A | 3/1992 | Krishnamurthy |
| 5,198,578 A | 3/1993 | Etzkorn et al. |
| 5,731,252 A | 3/1998 | Warner et al. |
| 6,147,126 A | 11/2000 | DeGeorge et al. |
| 6,392,078 B1 | 5/2002 | Ryu et al. |
| 6,492,535 B1 | 12/2002 | Castiglioni et al. |
| 6,573,340 B1 | 6/2003 | Khemani et al. |
| 6,773,578 B1 | 8/2004 | O'Rear et al. |
| 6,852,865 B2 | 2/2005 | Coates et al. |
| 6,916,951 B2 | 7/2005 | Tustin et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |

(Continued)

FOREIGN PATENT DOCUMENTS

| CN | 1771238 A | 5/2006 |
| CN | 103822811 A | 5/2014 |

(Continued)

OTHER PUBLICATIONS

Advisory Action received for U.S. Appl. No. 15/329,027, dated Jun. 28, 2018, 2 pages.

(Continued)

*Primary Examiner* — Brian E McDowell
(74) *Attorney, Agent, or Firm* — Young Basile Hanlon & MacFarlane, P.C.

(57) ABSTRACT

The present disclosure provides novel methods of making aluminum complexes with utility for promoting epoxide carbonylation reactions. Methods include reacting neutral metal carbonyl compounds with alkylaluminum complexes. For example, a compound of formula I:

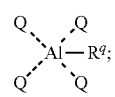

is reacted with a neutral metal carbonyl compound (such as $Q'_d M_e(CO)_{w'}$) to produce an aluminum-based carbonylation catalyst:

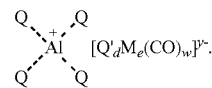

11 Claims, 2 Drawing Sheets

(56) References Cited

U.S. PATENT DOCUMENTS

| | | |
|---|---|---|
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 10,428,165 B2 | 10/2019 | Sookraj |
| 2003/0098274 A1 | 5/2003 | Lee et al. |
| 2003/0162961 A1 | 8/2003 | Coates et al. |
| 2004/0102532 A1 | 5/2004 | Landis et al. |
| 2005/0014977 A1 | 1/2005 | Drent et al. |
| 2005/0196343 A1 | 9/2005 | Reddy et al. |
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0301027 A1 | 12/2011 | Bitis et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0209775 A1 | 8/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0001946 A1 | 1/2017 | Sookraj |
| 2017/0002136 A1 | 1/2017 | Sookraj |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0002400 A1 | 1/2019 | Sookraj |
| 2019/0031592 A1 | 1/2019 | Sookraj et al. |
| 2019/0047972 A1 | 2/2019 | Sookraj |
| 2019/0071388 A1 | 3/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |
| 2019/0106533 A1 | 4/2019 | Sookraj |
| 2019/0255488 A1 | 8/2019 | Lapointe et al. |
| 2019/0255512 A1 | 8/2019 | Lee et al. |
| 2019/0256650 A1 | 8/2019 | Lee et al. |

FOREIGN PATENT DOCUMENTS

| | | |
|---|---|---|
| EP | 0352850 A1 | 1/1990 |
| EP | 0441447 A1 | 8/1991 |
| EP | 2325214 A1 | 5/2011 |
| GB | 762138 A | 11/1956 |
| JP | 57-14596 A | 1/1982 |
| WO | 2002/009781 A2 | 2/2002 |
| WO | 2006/087556 A1 | 8/2006 |
| WO | 2010/118128 A1 | 10/2010 |
| WO | 2010/137974 A1 | 12/2010 |
| WO | 2011/123558 A1 | 10/2011 |
| WO | 2011/163309 A2 | 12/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/067460 A1 | 5/2013 |
| WO | 2013/068846 A1 | 5/2013 |
| WO | 2013/122905 A1 | 8/2013 |
| WO | 2013/126375 A1 | 8/2013 |
| WO | 2013/180659 A1 | 12/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/110321 A1 | 7/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/004455 A1 | 1/2017 |
| WO | 2017/004477 A2 | 1/2017 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |

(56) References Cited

FOREIGN PATENT DOCUMENTS

| WO | 2019/050649 | A1 | 3/2019 |
|---|---|---|---|
| WO | 2019/051184 | A1 | 3/2019 |
| WO | 2019/070981 | A1 | 4/2019 |
| WO | 2019/183284 | A1 | 9/2019 |
| WO | 2019/195168 | A1 | 10/2019 |

OTHER PUBLICATIONS

Final Office Action received for U.S. Appl. No. 15/329,027, dated May 4, 2018, 6 pages.
Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.
Ganji et al., "In Situ Generation of the Coatescatalyst: a Practical and Versatile Catalytic System for the Carbonylation of Meso-Epoxides", ChemInform Abstract, vol. 42, Issue 39, 2011, 1 page.
Getzler et al., "Synthesis of β-Lactones: A Highly Active and Selective Catalyst for Epoxide Carbonylation", Journal of the American Chemical Society. vol. 124, No. 7, 2002, pp. 1174-1175.
International Search Report and Written Opinion received for PCT Patent Application No. PCT/US2016/017875, dated May 6, 2016, 16 pages.
International Search Report and Written Opinion received for PCT Patent Application No. PCT/US2016/017844, dated May 6, 2016, 10 pages.
International Search Report and Written Opinion received for PCT Patent Application No. PCT/US13/25683, dated Apr. 23, 2013, 8 pages.
International Search Report and Written Opinion received for PCT Patent Application No. PCT/US17/23302, dated Jun. 5, 2017, 9 pages.
International Search Report and Written Opinion received for PCT Patent Application No. PCT/US17/23303, dated Jun. 7, 2017, 18 pages.
International Search Report and Written Opinion received for PCT Patent Application No. PCT/US2010/030230, dated Jun. 10, 2010, 17 pages.
International Search Report and Written Opinion received for PCT Patent Application No. PCT/US11/49125, dated Jan. 11, 2012, 10 pages.
International Search Report and Written Opinion received for PCT Patent Application No. PCT/US2012/037675, dated Aug. 9, 2012, 12 pages.
International Search Report and Written Opinion received for PCT Patent Application No. PCT/US2012/061791, dated Feb. 8, 2013, 10 pages.
International Search Report and Written Opinion received for PCT Patent Application No. PCT/US2013/026810, dated Apr. 30, 2013, 8 pages.
International Search Report and Written Opinion received for PCT Patent Application No. PCT/US2013/048238, dated Dec. 3, 2013, 8 pages.
International Search Report and Written Opinion received for PCT Patent Application No. PCT/US2013/049026, dated Dec. 17, 2013, 9 pages.
International Search Report and Written Opinion received for PCT Patent Application No. PCT/US2014/069066, dated Mar. 16, 2015, 10 pages.
International Search Report and Written Opinion received for PCT Patent Application No. PCT/US2015/020562, dated Jun. 18, 2015, 9 pages.
International Search Report and Written Opinion received for PCT Patent Application No. PCT/US2015/028123, dated Jul. 23, 2015, 7 pages.
International Search Report and Written Opinion received for PCT Patent Application No. PCT/US2015/033232, dated Aug. 19, 2015, 8 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
International Search Report and Written Opinion received for PCT Patent Application No. PCT/US2017/059249, dated Feb. 22, 2018, 11 pages.
International Search Report and Written Opinion received for PCT Patent Application No. PCT/US2015/042124, dated Dec. 15, 2015, 14 pages.
International Preliminary Examination Report received for PCT Patent Application No. PCT/US2015/042124, dated Feb. 9, 2017, 10 pages.
Non-Final Office Action received for U.S. Appl. No. 15/329,027, dated Jan. 8, 2018, 12 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Stanghellini et al., "Redox Reactions of Metal Carbonyls. I. Kinetics and Mechanism of Disproportionation of Co2 (Co)8 with Piperidine", Inorganica Chimica Acta, vol. 22, 1977, pp. 19-22.
Slowik et al., "Catalytic Conversion of Waste Carbon Monoxide to Valuable Chemicals & Materials", Clean Technology, 2010, pp. 283-286.
Trimm, D. L., "Minimisation of Carbon Monoxide in a Hydrogen Stream for Fuel Cell Application", Applied Catalysis A: General, vol. 296, 2005, pp. 1-11.
"Understanding Biobased Carbon Content", Society of the Plastics Industry Bioplastics Council, Feb. 2012, pp. 1-12.

SYNTHESIS OF METAL COMPLEXES AND USES THEREOF

CROSS REFERENCE TO RELATED APPLICATIONS

The present invention is a continuation application of U.S. patent application Ser. No. 15/329,027, filed Jan. 25, 2017, which is a U.S. national phase patent application of PCT/US2015/042124, filed Jul. 24, 2015, which claims priority to U.S. Provisional Patent Application No. 62/028,993, filed Jul. 25, 2014, the entire contents of which are hereby incorporated by reference.

ACKNOWLEDGMENT OF GOVERNMENT SUPPORT

This invention was made with Government support under Grant No. DE-EE0005766, awarded by the Department of Energy. The government has certain rights in the invention.

BACKGROUND OF THE INVENTION

Bimetallic complexes containing a cationic metal-centered Lewis acid in combination with an anionic metal carbonyl are highly active catalysts for the ring-expanding carbonylation of strained heterocycles, including epoxides, aziridines, oxetanes and lactones. In particular, such bimetallic catalysts comprising a cationic aluminum complex as a Lewis-acidic component and a carbonyl cobaltate anion are useful for the double carbonylation of epoxides to succinic anhydrides (Rowley et al., *J. Am. Chem. Soc.,* 2007, 129, 4948-4960).

The syntheses of such aluminum carbonyl cobaltate complexes reported to date in the literature rely on a salt metathesis reaction performed by treating a chloroaluminum complex with a cobalt tetracarbonyl alkali metal salt to produce the desired aluminum cobaltate catalyst along with alkali metal chloride. Unfortunately, this procedure has features that make its implementation on large scale impractical. Firstly, the alkali metal salt of the carbonyl cobaltate utilized for the synthesis is not commercially available and must be formed in a separate step (typically from dicobalt octacarbonyl) then isolated and purified prior to use. In addition, the final catalyst product must be purified to remove residual alkali metal salts. Typically, this is done by recrystallizing the air sensitive catalyst which, while practicable at laboratory scale, is problematic at production volumes. As such, there remains a need for methods of making aluminum carbonyl cobaltate complexes that are practical and efficient for large-scale use.

SUMMARY OF THE INVENTION

In one aspect, the present invention provides methods of synthesizing ionic aluminum-based carbonylation catalysts.

In certain embodiments, the present invention provides methods for preparing an aluminum-based carbonylation catalyst of formula:

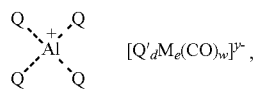

the method comprising a step of contacting a compound of formula I:

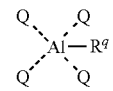

with a neutral metal carbonyl compound, where each of Q, $R^q$, M, Q', d, e, w, and y is as defined below and in the classes and subclasses herein.

In certain embodiments, the present invention provides methods for preparing an aluminum-based carbonylation catalyst of formula:

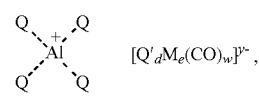

the method comprising a step of contacting a compound of formula I':

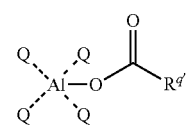

with a neutral metal carbonyl compound, where each of Q, $R^{q'}$, M, Q', d, e, w, and y is as defined below and in the classes and subclasses herein.

In another aspect, the present invention provides methods of synthesizing neutral aluminum-based carbonylation catalysts.

In certain embodiments, the present invention provides methods for preparing an aluminum-based carbonylation catalyst of formula:

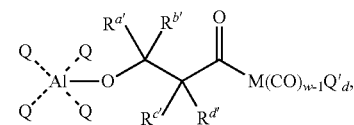

the method comprising a step of contacting a compound of formula I:

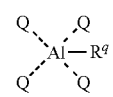

with a neutral metal carbonyl compound in the presence of carbon monoxide and an epoxide of formula:

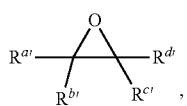

where each of Q, M, Q', $R^q$, $R^{a'}$, $R^{c'}$, $R^{d'}$, w, and d are as defined above and in the classes and subclasses herein.

In certain embodiments, the present invention provides methods for preparing an aluminum-based carbonylation catalyst of formula:

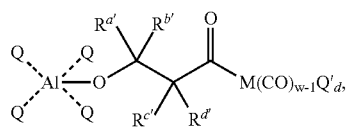

the method comprising a step of contacting a compound of formula I':

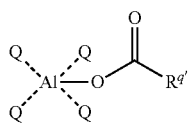

with a neutral metal carbonyl compound in the presence of carbon monoxide and an epoxide of formula:

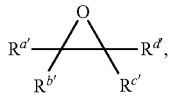

where each of Q, M, Q', $R^q$, $R^{a'}$, $R^{b'}$, $R^{c'}$, $R^{d'}$, w, and d are as defined above and in the classes and subclasses herein, In another aspect, the present invention encompasses methods for providing carbonylation catalysts to an epoxide carbonylation reaction. In certain embodiments of such methods, the epoxide carbonylation reaction comprises a reaction zone where an epoxide (or mixture of two or more epoxides) is contacted with carbon monoxide. In certain embodiments, such methods entail feeding the reaction zone with carbonylation catalyst by providing two separate catalyst feed streams: a first catalyst feed stream containing a compound of formula I or I' (as defined above and in the classes and subclasses herein) and a second catalyst feed stream containing a neutral metal carbonyl compound (as defined above and in the classes and subclasses herein).

In another aspect, the present invention encompasses methods for the synthesis of symmetrical ketones.

In certain embodiments, such methods comprise the step of contacting an aluminum compound of formula I:

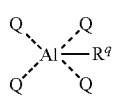

with a neutral metal carbonyl compound (as defined below and in the classes and subclasses herein) to provide a product having a formula:

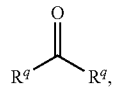

where each of Q and R' are as defined below and in the classes and subclasses herein.

DEFINITIONS

Figure 1:
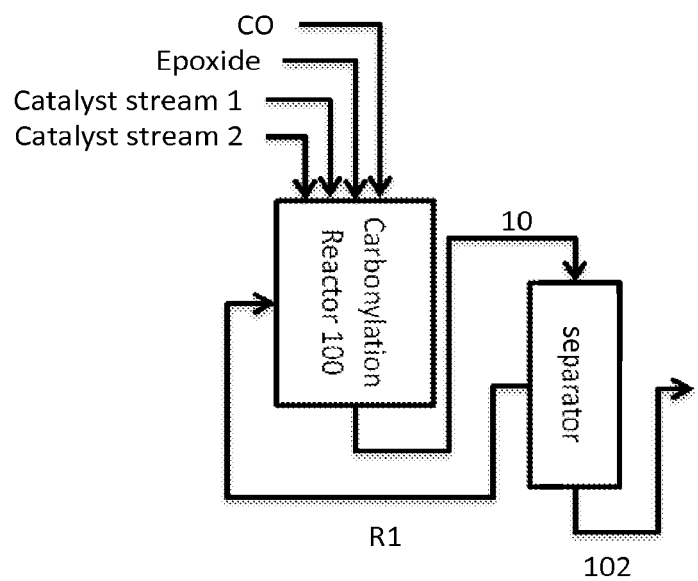
FIG. 1 shows a representative process schematic of a disclosed continuous carbonylation method where a first catalyst feed stream and second catalyst feed stream are fed directly to a continuous carbonylation reactor.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl, or (cycloalkyl)alkenyl.

The term "heteroaliphatic" or "heteroaliphatic group", as used herein, denotes an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. The term "heteroatom" refers to nitrogen, oxygen, or sulfur, and includes any oxidized form of nitrogen or sulfur, and any quaternized form of a basic nitrogen. The term "nitrogen" also includes a substituted nitrogen. Unless otherwise specified, heteroaliphatic groups contain 1-6 carbon atoms wherein 1-3 carbon atoms are optionally and independently replaced with heteroatoms selected from oxygen, nitrogen, and sulfur. In some embodiments, heteroaliphatic groups contain 1-4 carbon atoms, wherein 1-2 carbon atoms are optionally and independently replaced with heteroatoms selected from oxygen, nitrogen, and sulfur. In yet other embodiments, heteroaliphatic groups contain 1-3 carbon atoms, wherein 1 carbon atom is optionally and independently replaced with a heteroatom selected from oxygen, nitrogen, and sulfur. Suitable heteroaliphatic groups include, but are not limited to, linear or branched, heteroalkyl, heteroalkenyl, and heteroalkynyl groups.

The term "epoxide", as used herein, refers to a substituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated monocyclic, bicyclic, or polycyclic ring systems, as described herein, having from 3 to 20 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, bicyclo[2.2.1]heptyl, norbornyl, spiro[4.5]decyl, and cyclooctadienyl. In some embodiments, a cycloaliphatic group has 3-6 carbons. The terms "cycloaliphatic", "carbocycle", or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In certain embodiments, the term "$C_3$-$C_{14}$ carbocycle" refer to a 3- to 8-membered saturated or partially unsaturated monocyclic carbocyclic ring, or a 7- to 14-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_6$-$C_{10}$ aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroaralkyl" refers to an alkyl group substituted by a heteroaryl, wherein the alkyl and heteroaryl portions independently are optionally substituted. In certain embodiments, the terms "5- to 10-membered heteroaryl" and "$C_5$-$C_{10}$ heteroaryl" refer to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur.

As used herein, the terms "heterocyclyl," "heterocyclic radical," and "heterocyclic ring" are used interchangeably and refer to a stable 3- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur, or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "$C_3$-$C_{14}$ heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. It will be appreciated that this indicates that one or more of the substituents may be attached to the ring at any available position (usually in place of a hydrogen atom of the parent structure). In cases where an atom of a ring so substituted has two substitutable positions, two groups may be present on the same ring atom. Unless otherwise indicated, when more than one substituent is present, each is defined independently of the others, and each may have a different structure. In cases where the substituent shown crossing a bond of the ring is, e.g., "—R", this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N^+(R^\circ)_3$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}SR^\circ$; —SC(S)SR$^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)SR$^\circ$; —$(CH_2)_{0-4}OC(O)NR^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —$(CH_2)_{0-4}SSR^\circ$; —$(CH_2)_{0-4}S(O)_2R^\circ$; —$(CH_2)_{0-4}S(O)_2OR$; —$(CH_2)_{0-4}OS(O)_2R$; —S(O)$_2$NR$^\circ_2$; —$(CH_2)_{0-4}S(O)R^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —($C_{1-4}$ straight or branched alkylene)O—N(R$^\circ$)$_2$; or —($C_{1-4}$ straight or branched alkylene)C(O)O—N(R$^\circ$)$_2$, wherein each R$^\circ$ may be substituted as defined below and is independently hydrogen, $C_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-4}C(O)N(R^o)_2$; —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —C(O)$SR^{\bullet}$, —($C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NN$R^*_2$, =NNHC(O)$R^*$, =NNHC(O)O$R^*$, =NNHS(O)$_2R^*$, =N$R^*$, =NO$R^*$, —O(C($R^*_2$))$_{2-3}$O—, or —S(C($R^*_2$))$_{2-3}$S—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C$R^*_2$)$_{2-3}$O—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —O$R^{\bullet}$, —O(halo$R^{\bullet}$), —CN, —C(O)OH, —C(O)O$R^{\bullet}$, —$NH_2$, —NH$R^{\bullet}$, —N$R^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —C(O)$R^{\dagger}$, —C(O)O$R^{\dagger}$, —C(O)C(O)$R^{\dagger}$, —C(O)$CH_2C(O)R^{\dagger}$, —S(O)$_2R^{\dagger}$, —S(O)$_2NR^{\dagger}_2$, —C(S)$NR^{\dagger}_2$, —C(NH)$NR^{\dagger}_2$, or —N($R^{\dagger}$)S(O)$_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^1$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three $R^{\dagger}$ substituents to provide a charged ammonium moiety —N+($R^{\dagger}$)$_3$, wherein the ammonium moiety is further complexed with a suitable counterion.

Suitable substituents on the aliphatic group of $R^{\dagger}$ are independently halogen, —$R^{\bullet}$, -(halo$R^{\bullet}$), —OH, —OR, —O(halo$R^{\bullet}$), —CN, —C(O)OH, —C(O)OR, —$NH_2$, —NH$R^{\bullet}$, —N$R^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

Detailed Description of Certain Embodiments

I. Methods of Making Ionic Aluminum-Based Carbonylation Catalysts

In one aspect, the present invention provides methods of synthesizing ionic aluminum-based carbonylation catalysts.

I(a) Methods Based on Aluminum Alkyls and Aryls

In certain embodiments, the present invention provides methods for preparing an aluminum-based carbonylation catalyst of formula:

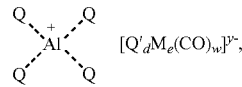

the method comprising a step of contacting a compound of formula I:

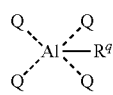

with a neutral metal carbonyl compound, where
Q is independently at each occurrence a nitrogen or oxygen atom which is part of a ligand complexed to the aluminum atom, where any two or more Q groups may comprise part of a single ligand;
$R^q$ is selected from optionally substituted $C_{1-12}$ aliphatic and optionally substituted aryl;
M is a metal atom;
Q' is any ligand and need not be present;
d is an integer between 0 and 8 inclusive;
e is an integer between 1 and 6 inclusive;
w is a number such as to provide the stable anionic metal carbonyl complex; and
y is the charge of the metal carbonyl anion.

In certain embodiments, the metal carbonyl anion in the aluminum-based carbonylation catalyst produced in the methods above comprises a monoanionic carbonyl complex of any metal from group 5, 7, or 9 of the periodic table or a dianionic carbonyl complex of any metal from group 4 or 8 of the periodic table. It should be understood that in cases where the metal carbonyl anion is dianionic, there will typically be two aluminum complexes associated with each dianionic metal carbonyl. In some embodiments, the metal carbonyl anion contains cobalt or manganese. In some embodiments, the metal carbonyl anion contains rhodium. Exemplary metal carbonyl anions include, but are not limited to: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In certain embodiments, the metal carbonyl anion comprises $[Co(CO)_4]^-$. In some embodiments, a mixture of two or more metal carbonyl anions may be present.

The term "such as to provide a stable anionic metal carbonyl" for w in metal carbonyl anions of formula $[Q'_dM_e(CO)_w]^{y-}$ is used herein to mean that $[Q'_dM_e(CO)_w]^{y-}$ is a species characterizable by analytical means, e.g., NMR, IR, X-ray crystallography, Raman spectroscopy and/or electron spin resonance (EPR) or isolable in the presence of a suitable cation, or a species formed in situ. It is to be understood that metals which can form stable metal carbonyl complexes have known coordinative capacities and propensities to form polynuclear complexes which, together with the number and character of optional ligands Q' that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl anions described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp (e.g., cyclopentadienyl). In certain embodiments, Q' is cp* (e.g., pentamethylcyclopentadienyl).

As described above, $R^q$ is an optionally substituted aliphatic group or aryl group. In certain embodiments, $R^q$ is a $C_{1-12}$ aliphatic group. In certain embodiments, $R^q$ is a $C_{1-8}$ aliphatic group. In certain embodiments, $R^q$ is a $C_{1-6}$ aliphatic group. In certain embodiments, $R^q$ is a $C_{1-4}$ aliphatic group.

In certain embodiments, $R^q$ is selected from the group consisting of methyl, ethyl, n-propyl, i-propyl, n-butyl, i-butyl, and octyl. In certain embodiments, $R^q$ is methyl. In certain embodiments, $R^q$ is ethyl. In certain embodiments, $R^q$ is i-propyl. In certain embodiments, $R^q$ is i-butyl. In certain embodiments, $R^q$ is n-butyl. In certain embodiments, $R^q$ is n-hexyl. In certain embodiments, $R^q$ is n-octyl. In certain embodiments, $R^q$ is ethyl. In certain embodiments, $R^q$ is methyl.

In certain embodiments, $R^q$ corresponds to an alkyl group of an available trialkyl aluminum compound. Several trialkylaluminum reagents are commercially available and processes for the preparation trialkylaluminum reagents are well known in the art: for example, by methods described in U.S. Pat. Nos. 3,006,942 and 3,960,912 (the contents of each of which are incorporated herein by reference). In some embodiments, a trialkylaluminum reagent is trimethylaluminum. In some embodiments, a trialkylaluminum reagent is triethylaluminum. In some embodiments, a trialkylaluminum reagent is tripropylaluminum. In some embodiments, a trialkylaluminum reagent is triisobutylaluminum. In some embodiments, a trialkylaluminum reagent is trioctylaluminum. In certain embodiments, the step of contacting the compound of formula I with a neutral metal carbonyl is performed in the presence one or more solvents. In certain embodiments, the provided organic solvent is selected from aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, the organic solvent comprises an ether. In certain embodiments, an ether is selected from diethyl ether, methy-t-butyl ether, tetrahydrofuran, 1,4-dioxane, glyme, diglyme, triglyme, higher glymes, or mixtures of any two or more of these. In certain embodiments, the organic solvent comprises a hydrocarbon. In certain embodiments, the hydrocarbon is a $C_{5-20}$ aliphatic hydrocarbon solvent. In certain embodiments, the aliphatic hydrocarbon is selected from pentanes, hexanes, heptanes, and mixtures of higher aliphatic hydrocarbons. In certain embodiments, the hydrocarbon is an aromatic hydrocarbon solvent. In certain embodiments, the aromatic hydrocarbon is selected from benzene, toluene, xylenes, mesitylene, halogenated aromatics, and compositions comprising mixtures of aromatic hydrocarbons.

In certain embodiments where the contacting step is performed in the presence of a solvent, one or both of compound I and the metal carbonyl are provided as solutions in the organic solvent. In certain embodiments, compound I and the metal carbonyl are each provided as solutions in the same solvent or mixture of solvents. In certain embodiments, compound I and the metal carbonyl are both provided as solutions in an ether. In certain embodiments, compound I and the metal carbonyl are both provided as solutions in 1,4-dioxane. In certain embodiments, compound I and the metal carbonyl are both provided as solutions in tetrahydrofuran. In certain embodiments, compound I and the metal carbonyl are both provided as solutions in diglyme.

In certain embodiments where the contacting step is performed in a hydrocarbon solvent, compound I is at least partially insoluble and is present as a suspension or slurry. In certain embodiments, the metal carbonyl compound is substantially soluble in the hydrocarbon solvent. In certain embodiments, where compound I is present as a slurry or suspension, the product catalyst is obtained as an insoluble solid.

In certain embodiments where the contacting step is performed in the presence of a solvent, the product of the method is a homogenous solution of the aluminum cobaltate catalyst. In certain embodiments where the contacting step is performed in the presence of a solvent, the method comprises one or more additional steps to isolate the catalyst. Such isolation processes are well known in the art and may include steps such removing solvent, crystallizing the product, precipitating the product, extracting the product, or combinations of any two or more of these.

In certain embodiments, a neutral metal carbonyl compound provided in any of the methods herein has the general formula $Q'_dM_e(CO)_{w'}$, where each Q', M, d, and e, is as defined above and in the classes and subclasses herein and w' is a number such as to provide a stable neutral metal carbonyl complex. In certain embodiments, a neutral metal carbonyl has the general formula $Q'M(CO)_{w'}$. In certain embodiments, a neutral metal carbonyl has the general formula $M(CO)_{w'}$. In certain embodiments, a neutral metal carbonyl has the general formula $Q'M_2(CO)_{w'}$. In certain embodiments, a neutral metal carbonyl has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$. The term "such as to provide a stable neutral metal carbonyl" for $Q'_dM_e$ $(CO)_{w'}$ is used herein to mean that $Q'_dM_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the neutral metal carbonyl compounds described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp. In certain embodiments, Q' is cp*.

In certain embodiments, a provided neutral metal carbonyl compound in the methods herein comprises a cobalt carbonyl compound. In certain embodiments, a provided neutral metal carbonyl compound is $Co_2(CO)_8$. In certain embodiments, a provided neutral metal carbonyl compound is $Co_4(CO)_{12}$. In certain embodiments, a provided neutral metal carbonyl compound is a mixture of two or more cobalt carbonyl species.

Therefore, in certain embodiments, the present invention provides methods for preparing an aluminum-based carbonylation catalyst of formula:

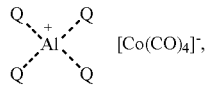

the method comprising a step of contacting a compound of formula I:

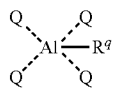

with a neutral cobalt carbonyl compound,
where each of Q and $R^q$ is as defined above and in the classes and subclasses herein.

In certain embodiments, the molar ratio of compound I to the neutral metal carbonyl compound is in the range of from about 0.1:1 to about 10:1. In certain embodiments, the molar ratio of compound I to the neutral metal carbonyl compound is in the range of from 0.1:1 to 2:1; or from 0.5:1 to 1.5:1; or from 0.7:1 to 1.5:1; or from 0.8:1 to 1.2:1; or from 0.9:1 to 1.1:1. In certain embodiments, the molar ratio of compound I to the neutral metal carbonyl compound is in the range of from 1:1 to 5:1; or from 1:1 to 4:1; or from 1:1 to 3:1; or from 1:1 to 2:1; or from 1.2:1 to 2.5:1; or from 1.4:1 to 2:1; or from 1.2:1 to 2:1; or from 1.5:1 to 2:1.

In certain embodiments, the molar ratio of compound I to a neutral metal carbonyl compound is controlled in the methods herein such that the molar ratio of metal atoms in a provided neutral metal carbonyl compound to aluminum atoms in a provided compound I is in the range of about 0.5:1 to about 2:1. For example, if a neutral metal carbonyl compound is dicobalt octacarbonyl, and compound I is an aluminum porphyrin complex, a 1:2 molar ratio of a neutral metal carbonyl to compound I would provide a 1:1 molar ratio of cobalt to aluminum atoms. In certain embodiments, the molar ratio of metal atoms in a provided neutral metal carbonyl compound to aluminum atoms in a provided compound I is in the range of from about 0.5:1 to about 1.5:1, or from about 0.7:1 to about 1.3:1, or from about 0.8:1 to about 1.2:1, or from about 0.9:1 to about 1.2:1, or from about 0.9:1 to about 1.1:1, or from about 0.95:1 to about 1.05:1. In certain embodiments, the molar ratio of metal atoms in a provided neutral metal carbonyl compound to aluminum atoms in a provided compound I is in the range of from about 1:1 to about 2:1, or from about 1:1 to about 1.8:1, or from about 1:1 to about 1.5:1, or from about 1:1 to about 1.4:1, or from about 1:1 to about 1.3:1, or from about 1:1 to about 1.2:1 or from about 1:1 to about 1.1:1.

In certain embodiments, the molar ratio of compound I to a neutral metal carbonyl compound is controlled in the methods herein such that the molar ratio of metal atoms in a provided neutral metal carbonyl compound to aluminum atoms in the provided compound I is about 1:1.

In certain embodiments, the step of contacting a compound of formula I with a neutral metal carbonyl compound entails adding compound I to a vessel containing a neutral metal carbonyl compound. In certain embodiments, compound I is added to the vessel as a solution in an organic solvent (vide supra). In certain embodiments, a neutral metal carbonyl present in the vessel to which compound I is added is present as a solution in an organic solvent. In certain embodiments, compound I is added as a solid or a slurry to the vessel containing a neutral metal carbonyl compound. In certain embodiments, a neutral metal carbonyl compound is present as a solid or a slurry in the vessel to which compound I is added.

In certain embodiments, the step of contacting a compound of formula I with a neutral metal carbonyl compound entails adding the neutral metal carbonyl compound to a vessel containing compound I. In certain embodiments, a neutral metal carbonyl compound is added to the vessel as a solution in an organic solvent (vide supra). In certain embodiments, compound I is present in the vessel to which a neutral metal carbonyl compound is added as a solution in an organic solvent. In certain embodiments, a neutral metal carbonyl compound is added as a solid or a slurry to the vessel containing the compound of formula I. In certain embodiments, a compound of formula I is present as a solid or a slurry in the vessel to which the neutral metal carbonyl compound is added.

In certain embodiments, the step of contacting a compound of formula I with a neutral metal carbonyl compound entails simultaneously adding the neutral metal carbonyl compound and compound I to a vessel. In certain embodiments, a neutral metal carbonyl compound is added to the vessel as a solution in an organic solvent (vide supra). In certain embodiments, a neutral metal carbonyl compound is added to the vessel as a solid or a slurry. In certain embodiments, compound I is added to the vessel as a solution in an organic solvent (vide supra). In certain embodiments, compound I is added to the vessel as a solid or a slurry. In certain embodiments, compound I and a neutral metal carbonyl are each added to the vessel as solutions in an organic solvent. In certain embodiments, the solutions are combined enroute to the vessel—e.g. by using a mixing tee or flowing the combined solutions through a static mixer.

In certain embodiments, compound I and a neutral metal carbonyl compound are contacted under an atmosphere comprising CO. In certain embodiments, the CO is present at a pressure from about 1 atmosphere to about 400 atmospheres. In certain embodiments, compound I and a neutral metal carbonyl compound are contacted under an atmosphere comprising CO at a pressure between about 1 atmosphere and about 100 atmospheres, or between about 1 atmosphere and about 50 atmospheres, or between about 10 atmospheres and about 20 atmospheres, or between about 5 atmospheres and about 10 atmospheres, or between about 1 atmosphere and about 5 atmospheres.

In certain embodiments, the step of contacting compound I with a neutral metal carbonyl includes heating. In certain embodiments, the contacting step is performed at a temperature between about 30° C. and about 250° C. In certain embodiments, the contacting step is performed at between 30 and 200 OC, between 30 and 150 OC, between 30 and 100 OC, between 30 and 80° C., between 40 and 100° C., between 50 and 100° C., between 100 and 200° C., between 100 and 150° C., or between 30 and 50° C.

In certain embodiments, the methods in section I(a) are characterized in that a product of the contacting step is a ketone of formula $(R^q)_2CO$ where $R^q$ is as defined above and in the classes and subclasses herein.

Therefore, in certain embodiments, the present invention encompasses a method of preparing an aluminum-based carbonylation catalyst of formula:

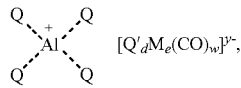

and a ketone of formula

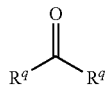

the method comprising a step of contacting a compound of formula I:

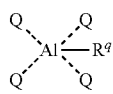

with a neutral metal carbonyl compound,
where each of Q, $R_q$, Q', M, d, e, w, and y is as defined above and in the classes and subclasses herein.

I(b) Methods Based on Aluminum Carboxylates

In certain embodiments, the present invention provides methods for preparing an aluminum-based carbonylation catalyst of formula:

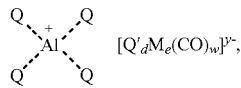

the method comprising a step of contacting a compound of formula I':

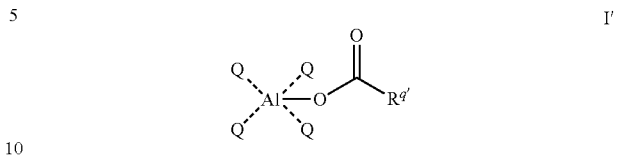

with a neutral metal carbonyl compound,
where each of Q, M, Q', d, e, w, and y is as defined above and in the classes and subclasses herein, and $R^{q'}$ is selected from —H, optionally substituted $C_{1-40}$ aliphatic and optionally substituted aryl.

In certain embodiments, the metal carbonyl anion ($[Q'_dM_e(CO)_w]^{y-}$) in the aluminum-based carbonylation catalyst produced in the methods above comprises a monoanionic carbonyl complex of any metal from group 5, 7 or 9 of the periodic table or a dianionic carbonyl complex of any metal from group 4 or 8 of the periodic table. It should be understood that in cases where the metal carbonyl anion is dianionic, there will typically be two aluminum complexes associated with each dianionic metal carbonyl. In some embodiments, the metal carbonyl anion contains cobalt or manganese. In some embodiments, the metal carbonyl anion contains rhodium. Exemplary metal carbonyl anions include, but are not limited to: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[FC_2(CO)_8]^{2-}$, $[Tc(CO)_5]^-$, $[Re(CO)_5]^-$, and $[Mn(CO)_5]^-$. In certain embodiments, the metal carbonyl anion comprises $[Co(CO)_4]^-$. In some embodiments, a mixture of two or more metal carbonyl anions may be present.

The term "such as to provide a stable anionic metal carbonyl" for w in metal carbonyl anions of formula $[Q'_dM_e(CO)_w]^{y-}$ is used herein to mean that $[Q'_dM_e(CO)_w]^{y-}$ is a species characterizable by analytical means, e.g., NMR, IR, X-ray crystallography, Raman spectroscopy and/or electron spin resonance (EPR) or isolable in the presence of a suitable cation, or a species formed in situ. It is to be understood that metals which can form stable metal carbonyl complexes have known coordinative capacities and propensities to form polynuclear complexes which, together with the number and character of optional ligands Q' that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl anions described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp. In certain embodiments, Q' is cp*.

As described above, $R^{q'}$ is selected from the group consisting of hydrogen, an optionally substituted aliphatic group or an optionally substituted aryl group. In certain embodiments, $R^{q'}$ is a $C_{1-40}$ aliphatic group. In certain embodiments, $R^{q'}$ is a $C_{1-20}$ aliphatic group. In certain embodiments, $R^{q'}$ is a $C_{1-8}$ aliphatic group. $R^q$ is a substituted $C_{1-8}$ aliphatic group. In certain embodiments, $R^{q'}$ is a $C_{1-12}$ aliphatic group. In certain embodiments, $R^q$ is a $C_{1-6}$ aliphatic group. In certain embodiments, $R^{q'}$ is a $C_{1-4}$ aliphatic group.

In certain embodiments, $R^{q'}$ is —H. In certain embodiments, $R^{q'}$ is selected from the group consisting of methyl, ethyl, n-propyl, i-propyl, n-butyl, i-butyl, and octyl. In certain embodiments, $R^{q'}$ is selected from the group consisting of chloromethyl, dichloromethyl, trichloromethyl, trifluoromethyl 1,1,1-trifluoromethyl, and pentafluoromethyl. In certain embodiments, $R^{q'}$ is methyl. In certain embodiments, $R^{q'}$ is ethyl. In certain embodiments, $R^{q'}$ is i-propyl. In certain embodiments, $R^{q'}$ is i-butyl. In certain embodiments, $R^{q'}$ is n-butyl. In certain embodiments, $R^{q'}$ is n-hexyl. In certain embodiments, $R^{q'}$ is n-octyl. In certain embodiments, $R^{q'}$ is a $C_{8-32}$ fatty acid chain.

In certain embodiments, $R^{q'}$ is an optionally substituted aromatic group. In certain embodiments, $R^{q'}$ is phenyl. In certain embodiments, $R^{q'}$ is selected from the group consisting of: phenyl, o-toluyl, m-toluyl, p-toluyl, chlorophenyl, and nitrophenyl. In certain embodiments, $R^{q'}$ is phenyl. In certain embodiments, $R^{q'}$ is substituted phenyl.

In certain embodiments, the step of contacting a compound of formula I' with a neutral metal carbonyl is performed in the presence of one or more solvents. In certain embodiments, the provided organic solvent is selected from aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, the organic solvent comprises an ether. In certain embodiments, an ether is selected from diethyl ether, methy-t-butyl ether, tetrahydrofuran, 1,4-dioxane, glyme, diglyme, triglyme, higher glymes, or mixtures of any two or more of these. In certain embodiments, the organic solvent comprises a hydrocarbon. In certain embodiments, the hydrocarbon is a $C_{5-20}$ aliphatic hydrocarbon solvent. In certain embodiments, the aliphatic hydrocarbon is selected from pentanes, hexanes, heptanes, and liquid mixtures of higher aliphatic hydrocarbons. In certain embodiments, the hydrocarbon is an aromatic hydrocarbon solvent. In certain embodiments, the aromatic hydrocarbon is selected from benzene, toluene, xylenes, mesitylene, halogenated aromatics, and compositions comprising mixtures of aromatic hydrocarbons.

In certain embodiments where the contacting step is performed in the presence of a solvent, one or both of compound I' and a metal carbonyl are provided as solutions in the organic solvent. In certain embodiments, compound I' and a metal carbonyl are each provided as solutions in the same solvent or mixture of solvents. In certain embodiments, compound I' and a metal carbonyl are both provided as solutions in an ether. In certain embodiments, compound I' and the metal carbonyl are both provided as solutions in 1,4-dioxane. In certain embodiments, compound I' and the metal carbonyl are both provided as solutions in tetrahydrofuran. In certain embodiments, compound I' and the metal carbonyl are both provided as solutions in diglyme.

In certain embodiments where the contacting step is performed in a hydrocarbon solvent, compound I' is at least partially insoluble and is present as a suspension or slurry. In certain embodiments, a metal carbonyl compound is substantially soluble in the hydrocarbon solvent. In certain embodiments, where compound I' is present as a slurry or suspension, a product catalyst is obtained as an insoluble solid.

In certain embodiments where the contacting step is performed in the presence of a solvent, the product of the method is a homogenous solution of the aluminum cobaltate catalyst. In certain embodiments where the contacting step is performed in the presence of a solvent, the method comprises one or more additional steps to isolate the catalyst. Such isolation processes are well known in the art and may include steps such as removing solvent, crystallizing the product, precipitating the product, extracting the product, or combinations of any two or more of these.

In certain embodiments, a neutral metal carbonyl compound provided in any of the methods herein has the general formula $Q'_d M_e (CO)_{w'}$, where each Q', M, d, and e, is as defined above and in the classes and subclasses herein and w' is a number such as to provide a stable neutral metal carbonyl complex. In certain embodiments, a neutral metal carbonyl has the general formula $Q'M(CO)_{w'}$. In certain embodiments, a neutral metal carbonyl has the general formula $M(CO)_{w'}$. In certain embodiments, a neutral metal carbonyl has the general formula $Q'M_2(CO)_{w'}$. In certain embodiments, a neutral metal carbonyl has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$.

The term "such as to provide a stable neutral metal carbonyl" for $Q'_d M_e (CO)_{w'}$ is used herein to mean that $Q'_d M_e (CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl compounds described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp (e.g., cyclopentadienyl). In certain embodiments, Q' is cp* (e.g., pentamethylcyclopentadienyl).

In certain embodiments, a provided neutral metal carbonyl compound in the methods herein comprises a cobalt carbonyl compound. In certain embodiments, a provided neutral metal carbonyl compound is $Co_2(CO)_8$. In certain embodiments, a provided neutral metal carbonyl compound is $Co_4(CO)_{12}$. In certain embodiments, a provided neutral metal carbonyl compound is a mixture of two or more cobalt carbonyl species.

Therefore, in certain embodiments, the present invention provides methods for preparing an aluminum-based carbonylation catalyst of formula:

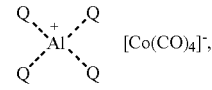

the method comprising a step of contacting a compound of formula I':

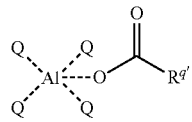

with a neutral cobalt carbonyl compound,
where each of Q and $R^{q'}$ is as defined above and in the classes and subclasses herein.

In certain embodiments, the molar ratio of compound I' to a neutral metal carbonyl compound is in the range of from about 0.1:1 to about 10:1. In certain embodiments, the molar ratio of compound I' to a neutral metal carbonyl compound is in the range of from 0.1:1 to 2:1; or from 0.5:1 to 1.5:1; or from 0.7:1 to 1.5:1; or from 0.8:1 to 1.2:1; or from 0.9:1 to 1.1:1. In certain embodiments, the molar ratio of compound I' to a neutral metal carbonyl compound is in the range of from 1:1 to 5:1; or from 1:1 to 4:1; or from 1:1 to 3:1; or from 1:1 to 2:1; or from 1.2:1 to 2.5:1; or from 1.4:1 to 2:1; or from 1.2:1 to 2:1; or from 1.5:1 to 2:1.

In certain embodiments, the molar ratio of compound I' to a neutral metal carbonyl compound is controlled in the methods herein such that the molar ratio of metal atoms in the provided neutral metal carbonyl compound to aluminum atoms in the provided compound I' is in the range of about 0.5:1 to about 2:1. For example, if a neutral metal carbonyl compound is dicobalt octacarbonyl, and compound I' is an aluminum porphyrin complex, a 1:2 molar ratio of a neutral metal carbonyl to compound I' would provide a 1:1 molar ratio of cobalt to aluminum atoms. In certain embodiments, the molar ratio of metal atoms in the provided neutral metal carbonyl compound to aluminum atoms in the provided compound I' is in the range of from about 0.5:1 to about 1.5:1, or from about 0.7:1 to about 1.3:1, or from about 0.8:1 to about 1.2:1, or from about 0.9:1 to about 1.2:1, or from about 0.9:1 to about 1.1:1, or from about 0.95:1 to about 1.05:1. In certain embodiments, the molar ratio of metal atoms in the provided neutral metal carbonyl compound to aluminum atoms in the provided compound I' is in the range of from about 1:1 to about 2:1, or from about 1:1 to about 1.8:1, or from about 1:1 to about 1.5:1, or from about 1:1 to about 1.4:1, or from about 1:1 to about 1.3:1, or from about 1:1 to about 1.2:1 or from about 1:1 to about 1.1:1.

In certain embodiments, the molar ratio of compound I' to a neutral metal carbonyl compound is controlled in the methods herein such that the molar ratio of metal atoms in the provided neutral metal carbonyl compound to aluminum atoms in the provided compound I' is about 1:1.

In certain embodiments, the step of contacting a compound of formula I' with a neutral metal carbonyl compound entails adding compound I' to a vessel containing a neutral metal carbonyl compound. In certain embodiments, compound I' is added to the vessel as a solution in an organic solvent (vide supra). In certain embodiments, a neutral metal carbonyl present in the vessel to which compound I' is added is present as a solution in an organic solvent. In certain embodiments, compound I' is added as a solid or a slurry to the vessel containing a neutral metal carbonyl compound. In certain embodiments, a neutral metal carbonyl compound is present as a solid or a slurry in the vessel to which compound I' is added.

In certain embodiments, the step of contacting a compound of formula I' with a neutral metal carbonyl compound entails adding the neutral metal carbonyl compound to a vessel containing compound I'. In certain embodiments, a neutral metal carbonyl compound is added to the vessel as a solution in an organic solvent (vide supra). In certain embodiments, compound I' is present in the vessel to which a neutral metal carbonyl compound is added as a solution in an organic solvent. In certain embodiments, a neutral metal carbonyl compound is added as a solid or a slurry to the vessel containing the compound of formula I'. In certain embodiments, a compound of formula I' is present as a solid or a slurry in the vessel to which a neutral metal carbonyl compound is added.

In certain embodiments, the step of contacting a compound of formula I' with a neutral metal carbonyl compound entails simultaneously adding a neutral metal carbonyl compound and compound I' to a vessel. In certain embodiments, a neutral metal carbonyl compound is added to the vessel as a solution in an organic solvent (vide supra). In certain embodiments, a neutral metal carbonyl compound is added to the vessel as a solid or a slurry. In certain embodiments, compound I' is added to the vessel as a solution in an organic solvent (vide supra). In certain embodiments, compound I' is added to the vessel as a solid or a slurry. In certain embodiments, compound I' and a neutral metal carbonyl are each added to the vessel as solutions in an organic solvent. In certain embodiments, the solutions are combined en route to the vessel—e.g. by using a mixing tee or flowing the combined solutions through a static mixer.

In certain embodiments, compound I' and a neutral metal carbonyl compound are contacted under an atmosphere comprising CO. In certain embodiments, the CO is present at a pressure from about 1 atmosphere to about 400 atmospheres. In certain embodiments, compound I' and a neutral metal carbonyl compound are contacted under an atmosphere comprising CO at a pressure between about 1 atmosphere and about 100 atmospheres, or between about 1 atmosphere and about 50 atmospheres, or between about 10 atmospheres and about 20 atmospheres, or between about 5 atmospheres and about 10 atmospheres, or between about 1 atmosphere and about 5 atmospheres.

In certain embodiments, the step of contacting compound I' with a neutral metal carbonyl includes heating. In certain embodiments, the contacting step is performed at a temperature between about 30° C. and about 250° C. In certain embodiments, the contacting step is performed at between 30 and 200° C., between 30 and 150° C., between 30 and 100° C., between 30 and 80° C., between 40 and 100° C., between 50 and 100° C., between 100 and 200° C., between 100 and 150° C., or between 30 and 50° C.

I(c) Contaminant Free Ionic Catalyst Compositions

In another aspect, the present invention encompasses the Applicant's recognition that catalysts made utilizing the salt metathesis methods of the prior art (described above) are contaminated with alkali metal salts and/or halides. Such contamination has been found to have undesirable effects in continuous reaction systems where it can lead to formation of precipitates that can foul pumps and/or interfere with catalyst recycling systems. Contrary to expectation, these contamination problems have been found to remain even after rigorous purification of catalysts made by salt metathesis (for example after recrystallization of the catalyst from organic solvents). In certain embodiments, the present invention encompasses methods of producing aluminum cobaltate catalysts that are essentially free of halide impurities and/or essentially free of alkali metal contaminants.

Therefore, in certain embodiments, the methods described above (e.g. those described in sections I(a) and I(b)) for preparing an aluminum-based carbonylation catalyst of formula:

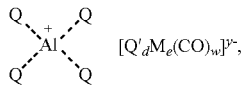

wherein each of Q, Q', M, d, e, w, and y is as defined above and described in classes and subclasses herein, are characterized in that the catalyst compositions thus formed have little or no contamination with halide and/or alkali metal salts. In certain embodiments, the methods are characterized in that the catalyst composition formed is essentially free of halide. In certain embodiments, the methods are characterized in that they provide a catalyst composition having a halide content less than about 200 ppm. In certain embodiments, the methods are characterized in that the catalyst composition formed has a halide content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. In certain embodiments, the methods are characterized in that the catalyst composition formed is essentially free of alkali metal salts. In certain embodiments, the methods are characterized in that the catalyst composition formed has an alkali metal salt content less than about 200 ppm. In certain embodiments, the methods are characterized in that the catalyst composition formed has an alkali metal salt content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. It will be appreciated that the amounts of halide or alkali metal salts in this paragraph refer to contaminant impurities or byproducts, not halogen atoms or counterions that are part of the desired catalyst.

II. Methods of Making Neutral Aluminum-Based Carbonylation Catalysts

In another aspect, the present invention provides methods of synthesizing neutral aluminum-based carbonylation catalysts.

II(a) Methods Based on Aluminum Alkyls or Aryls

In certain embodiments, the present invention provides methods for preparing an aluminum-based carbonylation catalyst of formula:

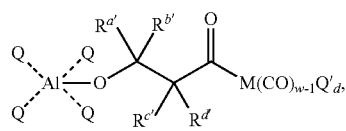

the method comprising a step of contacting a compound of formula I:

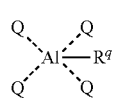

I with a neutral metal carbonyl compound in the presence of carbon monoxide and an epoxide of formula:

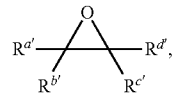

where each of Q, M, Q', $R^q$, w, and d are as defined above and in the classes and subclasses herein, $R^{a'}$ is hydrogen or an optionally substituted group selected from the group consisting of $C_{1-30}$ aliphatic; $C_{1-30}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-3 heteroatoms independently selected from the group consisting of nitrogen, oxygen, and sulfur; each of $R^{b'}$, $R^{c'}$, and $R^{d'}$ is independently hydrogen or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-3 heteroatoms independently selected from the group consisting of nitrogen, oxygen, and sulfur;

wherein any of ($R^{b'}$ and $R_c'$), ($R^{c'}$ and $R^{d'}$), and ($R^{a'}$ and $R^{b'}$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

In certain embodiments, a compound of formula I and a neutral metal carbonyl compound are contacted in the presence of an epoxide selected from the group consisting of: ethylene oxide, propylene oxide, 1,2 butylene oxide, 2,3 butylene oxide, epoxides of higher alpha olefins, epichlorohydrin, glycidyl ethers, cyclohexene oxide, cyclopentene oxide, 3-vinyl cyclohexene oxide, and 3-ethyl cyclohexene oxide.

In certain embodiments, a compound of formula I and a neutral metal carbonyl compound are contacted in the presence of ethylene oxide.

In certain embodiments, a compound of formula I and a neutral metal carbonyl compound are contacted in the presence of propylene oxide.

In certain embodiments, an epoxide is present in a molar excess relative to compound I and a neutral metal carbonyl compound. In certain embodiments, an epoxide is present in at least a 2-fold molar excess, at least a 5-fold molar excess, at least a 10-fold molar excess, at least a 20-fold molar excess, at least a 50-fold molar excess, at least a 100-fold molar excess, at least a 500-fold molar excess, or at least a 1,000-fold molar excess, relative to compound I or a neutral metal carbonyl compound.

In certain embodiments, a compound of formula I and a neutral metal carbonyl compound are contacted under CO pressure. In certain embodiments, the CO pressure is in the range from about 1 atmosphere to about 400 atmospheres. In certain embodiments, compound I and a neutral metal carbonyl compound are contacted under an atmosphere comprising CO at a pressure between about 2 atmospheres and about 100 atmospheres, or between about 5 atmosphere and about 50 atmospheres, or between about 10 atmospheres and about 20 atmospheres, or between about 20 atmospheres and about 50 atmospheres, or between about 50 atmospheres and about 100 atmospheres.

In certain embodiments of methods for synthesizing neutral aluminum-based carbonylation catalysts, a neutral metal carbonyl compound provided has the general formula $Q'_dM_e(CO)_{w'}$, where each Q', M, d, and e, is as defined above and in the classes and subclasses herein and w' is a number such as to provide a stable neutral metal carbonyl complex. In certain embodiments, a neutral metal carbonyl has the general formula $Q'M(CO)_{w'}$. In certain embodiments, a neutral metal carbonyl has the general formula $M(CO)_{w'}$. In certain embodiments, a neutral metal carbonyl has the general formula $Q'M_2(CO)_{w'}$. In certain embodiments, a neutral metal carbonyl has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$. The term "such as to provide a stable neutral metal carbonyl" for $Q'_dM_e(CO)_{w'}$ is used herein to mean that $Q'_dM_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds have stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl compounds described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp. In certain embodiments, Q' is cp*.

In certain embodiments, a provided neutral metal carbonyl compound in the methods comprises a cobalt carbonyl compound. In certain embodiments, a provided neutral metal carbonyl compound is $Co_2(CO)_8$. In certain embodiments, a provided neutral metal carbonyl compound is $Co_4(CO)_{12}$. In certain embodiments, a provided neutral metal carbonyl compound is a mixture of two or more cobalt carbonyl species.

In certain embodiments, the step of contacting the compound of formula I with a neutral metal carbonyl is performed in the presence one or more solvents in addition to the epoxide and CO. In certain embodiments, the provided organic solvent is selected from aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, the organic solvent comprises an ether. In certain embodiments, an ether is selected from diethyl ether, methy-t-butyl ether, tetrahydrofuran, 1,4-dioxane, glyme, diglyme, triglyme, higher glymes, or mixtures of any two or more of these.

In certain embodiments where the contacting step is performed in the presence of a solvent, one or both of compound I and a metal carbonyl are provided as solutions in the organic solvent. In certain embodiments, compound I and a metal carbonyl are each provided as solutions in the same solvent or mixture of solvents. In certain embodiments, compound I and a metal carbonyl are both provided as solutions in an ether. In certain embodiments, compound I and a metal carbonyl are both provided as solutions in 1,4-dioxane. In certain embodiments, compound I and a metal carbonyl are both provided as solutions in tetrahydrofuran. In certain embodiments, compound I and a metal carbonyl are both provided as solutions in diglyme.

In certain embodiments, a neutral metal carbonyl compound is provided as a solution in the epoxide.

In certain embodiments, the present invention provides methods for preparing an aluminum-based carbonylation catalyst of formula:

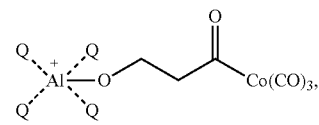

the method comprising the step of contacting a compound of formula I:

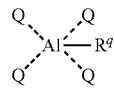

with a neutral cobalt carbonyl compound in the presence of ethylene oxide and carbon monoxide, where each of Q and $R^q$ is as defined above and in the classes and subclasses herein.

In certain embodiments, a neutral cobalt carbonyl compound comprises dicobalt octacarbonyl. In certain embodiments, a neutral cobalt carbonyl compound comprises tetracobalt dodecacarbonyl. In certain embodiments, a neutral cobalt carbonyl compound comprises a mixture of two or more cobalt carbonyl species.

In certain embodiments, the molar ratio of compound I to the neutral metal carbonyl compound is in the range of from about 0.1:1 to about 10:1. In certain embodiments, the molar ratio of compound I to the neutral metal carbonyl compound is in the range of from 0.1:1 to 2:1; or from 0.5:1 to 1.5:1; or from 0.7:1 to 1.5:1; or from 0.8:1 to 1.2:1; or from 0.9:1 to 1.1:1. In certain embodiments, the molar ratio of compound I to the neutral metal carbonyl compound is in the range of from 1:1 to 5:1; or from 1:1 to 4:1; or from 1:1 to 3:1; or from 1:1 to 2:1; or from 1.2:1 to 2.5:1; or from 1.4:1 to 2:1; or from 1.2:1 to 2:1; or from 1.5:1 to 2:1.

In certain embodiments, the molar ratio of compound I to the neutral metal carbonyl compound is controlled in the methods herein such that the molar ratio of metal atoms in the provided neutral metal carbonyl compound to aluminum atoms in the provided compound I is in the range of about 0.5:1 to about 2:1. For example, if the neutral metal carbonyl compound is dicobalt octacarbonyl, and compound I is an aluminum porphyrin complex, a 1:2 molar ratio of the neutral metal carbonyl to compound I would provide a 1:1 molar ratio of cobalt to aluminum atoms. In certain embodiments, the molar ratio of metal atoms in the provided neutral metal carbonyl compound to aluminum atoms in the provided compound I is in the range of from about 0.5:1 to about 1.5:1, or from about 0.7:1 to about 1.3:1, or from about 0.8:1 to about 1.2:1, or from about 0.9:1 to about 1.2:1, or from about 0.9:1 to about 1.1:1, or from about 0.95:1 to about 1.05:1. In certain embodiments, the molar ratio of metal atoms in the provided neutral metal carbonyl compound to aluminum atoms in the provided compound I is in the range of from about 1:1 to about 2:1, or from about 1:1 to about 1.8:1, or from about 1:1 to about 1.5:1, or from about 1:1 to about 1.4:1, or from about 1:1 to about 1.3:1, or from about 1:1 to about 1.2:1 or from about 1:1 to about 1.1:1.

In certain embodiments, the molar ratio of compound I to the neutral metal carbonyl compound is controlled in the methods herein such that the molar ratio of metal atoms in a provided neutral metal carbonyl compound to aluminum atoms in a provided compound I is about 1:1.

In certain embodiments, the step of contacting compound I with a neutral metal carbonyl includes heating. In certain embodiments, the contacting step is performed at a temperature between about 30° C. and about 100° C. In certain embodiments, the contacting step is performed at a temperature between 30 and 80° C., between 40 and 100° C., between 50 and 100° C., between 100 and 200° C., between 100 and 150° C., or between 30 and 50° C.

In certain embodiments, the methods in section II(a) are characterized in that a product of the contacting step is a ketone of formula $(R^q)_2CO$ where $R^q$ is as defined above and in the classes and subclasses herein.

Therefore, in certain embodiments, the present invention encompasses a method of preparing an aluminum-based carbonylation catalyst of formula:

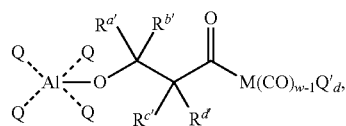

and a ketone of formula

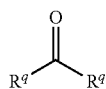

the method comprising a step of contacting a compound of formula I:

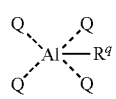

with a neutral metal carbonyl compound in the presence of carbon monoxide and an epoxide of formula:

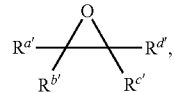

where each of Q, $R^q$, Q', $R^{a'}$, $R^{b'}$, $R^{c'}$, $R^{d'}$, d, e, w, and y is as defined above and in the classes and subclasses herein.

II(b) Methods Based on Aluminum Carboxylates

In certain embodiments, the present invention provides methods for preparing an aluminum-based carbonylation catalyst of formula:

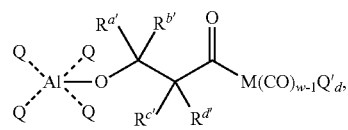

the method comprising a step of contacting a compound of formula I:

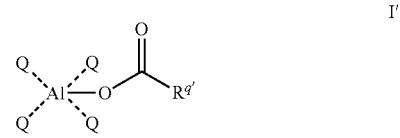

with a neutral metal carbonyl compound in the presence of carbon monoxide and an epoxide of formula:

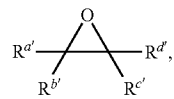

where each of Q, M, Q', $R^{q'}$, w, d, $R^{a'}$, $R^{b'}$, $R^{c'}$, and $R^{d'}$ are as defined above and in the classes and subclasses herein, In certain embodiments, a compound of formula I' and a neutral metal carbonyl compound are contacted in the presence of an epoxide selected from the group consisting of: ethylene oxide, propylene oxide, 1,2 butylene oxide, 2,3 butylene oxide, epoxides of higher alpha olefins, epichlorohydrin, glycidyl ethers, cyclohexene oxide, cyclopentene oxide, 3-vinyl cyclohexene oxide, and 3-ethyl cyclohexene oxide.

In certain embodiments, a compound of formula I' and a neutral metal carbonyl compound are contacted in the presence of ethylene oxide.

In certain embodiments, a compound of formula I' and a neutral metal carbonyl compound are contacted in the presence of propylene oxide.

In certain embodiments, an epoxide is present in a molar excess relative to compound I' and a neutral metal carbonyl compound. In certain embodiments, an epoxide is present in at least a 2-fold molar excess, at least a 5-fold molar excess, at least a 10-fold molar excess, at least a 20-fold molar excess, at least a 50-fold molar excess, at least a 100-fold molar excess, at least a 500-fold molar excess, at least a 1,000-fold molar excess, relative to compound I' or the neutral metal carbonyl compound.

In certain embodiments, a compound of formula I' and a neutral metal carbonyl compound are contacted under CO pressure. In certain embodiments, the CO pressure is in the range from about 1 atmosphere to to about 400 atmospheres. In certain embodiments, compound I' and a neutral metal carbonyl compound are contacted under an atmosphere comprising CO at a pressure between about 2 atmospheres and about 100 atmospheres, or between about 5 atmosphere and about 50 atmospheres, or between about 10 atmospheres and about 20 atmospheres, or between about 20 atmospheres and about 50 atmospheres, or between about 50 atmospheres and about 100 atmospheres.

In certain embodiments of methods for synthesizing neutral aluminum-based carbonylation catalysts, a neutral metal carbonyl compound provided has the general formula $Q'_d M_e (CO)_{w'}$, where each Q', M, d, and e, is as defined above and in the classes and subclasses herein and w' is a number such as to provide a stable neutral metal carbonyl complex. In certain embodiments, a neutral metal carbonyl has the general formula $Q'M(CO)_{w'}$. In certain embodiments, a neutral metal carbonyl has the general formula $M(CO)_{w'}$. In certain embodiments, a neutral metal carbonyl has the general formula $Q'M_2(CO)_{w'}$. In certain embodiments, a neutral metal carbonyl has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$. The term "such as to provide a stable neutral metal carbonyl" for $Q'_d M_e(CO)_{w'}$ is used herein to mean that $Q'_d M_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q' that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl compounds described above is replaced with a ligand Q'. In certain embodiments, Q' is a phosphine ligand. In certain embodiments, Q' is a triaryl phosphine. In certain embodiments, Q' is trialkyl phosphine. In certain embodiments, Q' is a phosphite ligand. In certain embodiments, Q' is an optionally substituted cyclopentadienyl ligand. In certain embodiments, Q' is cp. In certain embodiments, Q' is cp*.

In certain embodiments, a provided neutral metal carbonyl compound in the methods comprises a cobalt carbonyl compound. In certain embodiments, a provided neutral metal carbonyl compound is $Co_2(CO)_8$. In certain embodiments, a provided neutral metal carbonyl compound is $Co_4(CO)_{12}$. In certain embodiments, a provided neutral metal carbonyl compound is a mixture of two or more cobalt carbonyl species.

As described above, $R^{q'}$ is selected from the group consisting of hydrogen, an optionally substituted aliphatic group or an optionally substituted aryl group. In certain embodiments, $R^{q'}$ is a $C_{1-40}$ aliphatic group. In certain embodiments, $R^{q'}$ is a $C_{1-20}$ aliphatic group. In certain embodiments, $R^{q'}$ is a $C_{1-8}$ aliphatic group. $R^{q'}$ is a substituted $C_{1-8}$ aliphatic group. In certain embodiments, $R^{q'}$ is a $C_{1-12}$ aliphatic group. In certain embodiments, $R^q$ is a $C_{1-6}$ aliphatic group. In certain embodiments, $R^{q'}$ is a $C_{1-4}$ aliphatic group.

In certain embodiments, $R^{q'}$ is —H. In certain embodiments, $R^{q'}$ is selected from the group consisting of methyl, ethyl, n-propyl, i-propyl, n-butyl, i-butyl, and octyl. In certain embodiments, $R^{q'}$ is selected from the group consisting of chloromethyl, dichloromethyl, trichloromethyl, trifluoromethyl 1,1,1-trifluoromethyl, and pentafluoromethyl. In certain embodiments, $R^{q'}$ is methyl. In certain embodiments, $R^{q'}$ is ethyl. In certain embodiments, $R^{q'}$ is i-propyl. In certain embodiments, $R^{q'}$ is i-butyl. In certain embodiments, $R^{q'}$ is n-butyl. In certain embodiments, $R^{q'}$ is n-hexyl. In certain embodiments, $R^{q'}$ is n-octyl. In certain embodiments, $R^{q'}$ is a $C_{8-32}$ fatty acid chain.

In certain embodiments, $R^{q'}$ is an optionally substituted aromatic group. In certain embodiments, $R^q$ is phenyl. In certain embodiments, $R^{q'}$ is selected from the group consisting of: phenyl, o-toluyl, m-toluyl, p-toluyl chlorophenyl, and nitrophenyl. In certain embodiments, $R^{q'}$ is phenyl. In certain embodiments, $R^{q'}$ is substituted phenyl.

In certain embodiments, the step of contacting the compound of formula I' with a neutral metal carbonyl is performed in the presence one or more solvents in addition to the epoxide and CO. In certain embodiments, a provided organic solvent is selected from aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, an organic solvent comprises an ether. In certain embodiments, an ether is selected from diethyl ether, methy-t-butyl ether, tetrahydrofuran, 1,4-dioxane, glyme, diglyme, triglyme, higher glymes, or mixtures of any two or more of these.

In certain embodiments where the contacting step is performed in the presence of a solvent, one or both of compound I' and the metal carbonyl are provided as solutions in the organic solvent. In certain embodiments, compound I' and the metal carbonyl are each provided as solutions in the same solvent or mixture of solvents. In certain embodiments, compound I' and a metal carbonyl are both provided as solutions in an ether. In certain embodiments, compound I' and a metal carbonyl are both provided as solutions in 1,4-dioxane. In certain embodiments, compound I' and a metal carbonyl are both provided as solutions in tetrahydrofuran. In certain embodiments, compound I' and a metal carbonyl are both provided as solutions in diglyme.

In certain embodiments, a neutral metal carbonyl compound is provided as a solution in an epoxide.

In certain embodiments, the present invention provides methods for preparing an aluminum-based carbonylation catalyst of formula:

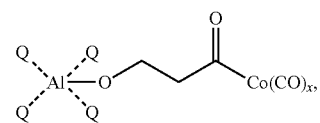

the method comprising the step of contacting a compound of formula I':

I'

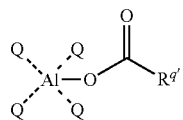

with a neutral cobalt carbonyl compound in the presence of ethylene oxide and carbon monoxide, where each of Q and $R^{q'}$ is as defined above and in the classes and subclasses herein, and x is such that a stable complex is formed. In some embodiments, x is 3.

In certain embodiments, a neutral cobalt carbonyl compound comprises dicobalt octacarbonyl. In certain embodiments, a neutral cobalt carbonyl compound comprises tetracobalt dodecacarbonyl. In certain embodiments, a neutral cobalt carbonyl compound comprises a mixture of two or more cobalt carbonyl species.

In certain embodiments, the molar ratio of compound I' to the neutral metal carbonyl compound is in the range of from about 0.1:1 to about 10:1. In certain embodiments, the molar ratio of compound I' to the neutral metal carbonyl compound is in the range of from 0.1:1 to 2:1; or from 0.5:1 to 1.5:1; or from 0.7:1 to 1.5:1; or from 0.8:1 to 1.2:1; or from 0.9:1 to 1.1:1. In certain embodiments, the molar ratio of compound I' to the neutral metal carbonyl compound is in the range of from 1:1 to 5:1; or from 1:1 to 4:1; or from 1:1 to 3:1; or from 1:1 to 3:1; or from 1:1 to 2:1; or from 1.2:1 to 2.5:1; or from 1.4:1 to 2:1; or from 1.2:1 to 2:1; or from 1.5:1 to 2:1.

In certain embodiments, the molar ratio of compound I' to the neutral metal carbonyl compound is controlled in the methods herein such that the molar ratio of metal atoms in the provided neutral metal carbonyl compound to aluminum atoms in the provided compound I' is in the range of about 0.5:1 to about 2:1. For example, if the neutral metal carbonyl compound is dicobalt octacarbonyl, and compound I' is an aluminum porphyrin complex, a 1:2 molar ratio of the neutral metal carbonyl to compound I' would provide a 1:1 molar ratio of cobalt to aluminum atoms. In certain embodiments, the molar ratio of metal atoms in the provided neutral metal carbonyl compound to aluminum atoms in the provided compound I' is in the range of from about 0.5:1 to about 1.5:1, or from about 0.7:1 to about 1.3:1, or from about 0.8:1 to about 1.2:1, or from about 0.9:1 to about 1.2:1, or from about 0.9:1 to about 1.1:1, or from about 0.95:1 to about 1.05:1. In certain embodiments, the molar ratio of metal atoms in the provided neutral metal carbonyl compound to aluminum atoms in the provided compound I' is in the range of from about 1:1 to about 2:1, or from about 1:1 to about 1.8:1, or from about 1:1 to about 1.5:1, or from about 1:1 to about 1.4:1, or from about 1:1 to about 1.3:1, or from about 1:1 to about 1.2:1 or from about 1:1 to about 1.1:1.

In certain embodiments, the molar ratio of compound I' to the neutral metal carbonyl compound is controlled in the methods herein such that the molar ratio of metal atoms in the provided neutral metal carbonyl compound to aluminum atoms in the provided compound I' is about 1:1.

In certain embodiments, the step of contacting compound I' with the neutral metal carbonyl includes heating. In certain embodiments, the contacting step is performed at a temperature between about 30° C. and about 100° C. In certain embodiments, the contacting step is performed at a temperature between 30 and 80° C., between 40 and 100° C., between 50 and 100° C., between 100 and 200° C., between 100 and 150° C., or between 30 and 50° C.

II(c) Contaminant-Free Neutral Catalyst Compositions

In certain embodiments, the methods described herein for preparing an aluminum-based carbonylation catalyst of formula:

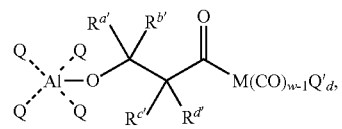

where each of Q, M, Q', w, d, $R^{a'}$, $R^{b'}$, $R^{c'}$, and $R^{d'}$ are as defined above and in the classes and subclasses herein, are characterized in that the catalysts thus formed have little or no contamination with halide and/or alkali metal salts. In certain embodiments, the methods are characterized in that the catalyst formed is essentially free of halide. In certain embodiments, the methods are characterized in that the catalyst composition formed has a halide content less than about 200 ppm. In certain embodiments, the methods are characterized in that the catalyst composition formed has a halide content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. In certain embodiments, the methods are characterized in that the catalyst composition formed is essentially free of alkali metal salts. In certain embodiments, the methods are characterized in that the catalyst composition formed has an alkali metal salt content less than about 200 ppm. In certain embodiments, the methods are characterized in that the catalyst formed has an alkali metal salt content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. It will be appreciated that the amounts of halide or alkali metal salts in this paragraph refer to contaminant impurities or byproducts, not halogen atoms or counterions that are part of the desired catalyst.

III. Methods for Providing Carbonylation Catalysts to Epoxide Carbonylation Reactions In another aspect, the present invention encompasses methods for providing carbonylation catalysts to an epoxide carbonylation reaction. In certain embodiments of such methods, the epoxide carbonylation reaction comprises a reaction zone where an epoxide (or mixture of two or more epoxides) is contacted with carbon monoxide. In certain embodiments, such methods entail feeding the reaction zone with carbonylation catalyst by providing two separate catalyst feed streams: a first catalyst feed stream containing a compound of formulae I or I' (as defined above and in the classes and subclasses herein) and a second catalyst feed stream containing a neutral metal carbonyl compound (as defined above and in the classes and subclasses herein).

In certain embodiments, such methods comprise feeding the reaction zone with a first catalyst feed stream containing a compound of formulae I or I' (as defined above and in the classes and subclasses herein) and a second catalyst feed stream containing a neutral cobalt carbonyl compound. In certain embodiments, such methods comprise feeding the reaction zone with a first catalyst feed stream containing a compound of formulae I or I' (as defined above and in the classes and subclasses herein) and a second catalyst feed stream containing dicobalt octacarbonyl. In certain embodiments, the first feed stream and the second feed stream are fed to the reaction zone at rates such that approximately equimolar amounts of cobalt and aluminum are fed to the reaction zone per unit time.

In certain embodiments, the epoxide carbonylation zone to which the two catalyst feed streams is fed is part of a continuous epoxide carbonylation process. In certain embodiments, the reaction zone comprises a continuous epoxide carbonylation reactor. In certain embodiments, the continuous carbonylation reactor comprises one or more continuous stirred tank reactors (CSTRs). In certain embodiments, the continuous carbonylation reactor comprises one or more plug flow reactors (PFRs). In certain embodiments, the continuous carbonylation reactor is also fed with an epoxide feed stream and carbon monoxide.

In certain embodiments where the reaction zone is a continuous epoxide carbonylation reactor, the continuous reactor is also fed with an epoxide feed stream and carbon monoxide. In some such embodiments, the first catalyst feed stream and the second catalyst feed stream are fed to the reaction zone at rates such that a molar ratio of epoxide to carbonylation catalyst fed to the continuous reactor per unit time is between about 10 and about 100,000 moles of epoxide per mole of carbonylation catalyst. In certain embodiments, the molar ratio of epoxide to carbonylation catalyst fed to the reactor per unit time is between about 50 and about 50,000, between about 100 and about 20,000, between about 100 and about 10,000, between about 100 and about 5,000, or between about 100 and about 2,500. In certain embodiments, the molar ratio of epoxide to carbonylation catalyst fed to the reactor per unit time is between about 100 and about 50,000, between about 100 and about 20,000, between about 100 and about 10,000, between about 100 and about 5,000, or between about 100 and about 2,500. In certain embodiments, the molar ratio of epoxide to carbonylation catalyst fed to the reactor per unit time is between about 200 and about 20,000, between about 500 and about 10,000, between about 500 and about 5,000, between about 1,000 and about 5,000, between about 2,000 and about 5,000 between about 2,000 and about 3,000, or between about 5,000 and about 10,000.

In certain embodiments, one or both of the first catalyst feedstream and the second catalyst feedstream comprises solvent. In certain embodiments, such feed streams comprise an organic solvent selected from the group consisting of: aliphatic hydrocarbons, aromatic hydrocarbons, halogenated solvents, ethers, esters, ketones, nitriles, amides, carbonates, alcohols, amines, sulfones, or mixtures of any two or more of these. In certain embodiments, such feed streams comprise one or more ethers. In certain embodiments, an ether is selected from diethyl ether, methy-t-butyl ether, tetrahydrofuran, 1,4-dioxane, glyme, diglyme, triglyme, higher glymes, or mixtures of any two or more of these. In certain embodiments, such feed streams comprise 1,4-dioxane. In certain embodiments, such feed streams comprise tetrahydrofuran. In certain embodiments, such feed streams comprise diglyme.

In certain embodiments, the first catalyst feed stream comprises a homogenous solution of an aluminum complex of formulae I or I' in an organic solvent. In certain embodiments, the first catalyst feed stream comprises a slurry of an aluminum complex of formulae I or I' in an organic solvent. In certain embodiments, the first catalyst feed stream comprises an ether. In certain embodiments, the first catalyst feed stream comprises 1,4-dioxane. In certain embodiments, such feed streams comprise tetrahydrofuran. In certain embodiments, such feed streams comprise diglyme.

In certain embodiments, the second catalyst feed stream comprises a homogenous solution of a neutral metal carbonyl compound in an organic solvent. In certain embodiments, the second catalyst feed stream comprises a slurry of a neutral metal carbonyl compound in an organic solvent. In certain embodiments, the second catalyst feed stream comprises an ether. In certain embodiments, the second catalyst feed stream comprises 1,4-dioxane. In certain embodiments, the second catalyst feed stream comprises a hydrocarbon solvent. In certain embodiments, the second catalyst feed stream comprises tetrahydrofuran. In certain embodiments, the second catalyst feed stream comprises diglyme.

In certain embodiments where at least one of the first or second carbonylation catalyst feed streams comprises an organic solvent, and where the epoxide carbonylation reaction is a continuous carbonylation process, the method is characterized in that there are no additional solvent feeds to the continuous reactor. Or put another way, the method is characterized in that all of the reaction solvent fed to the continuous epoxide carbonylation reaction is provided via the catalyst feed streams.

As mentioned above, one advantage of methods of the present invention is the ability to provide epoxide carbonylation catalysts that are essentially free of halide and/or alkali metal salt impurities. Therefore, in certain embodiments, the present invention encompasses methods for feeding the reaction zone of an epoxide carbonylation reaction with carbonylation catalyst characterized in that the epoxide carbonylation reaction zone remains essentially free of halide and/or alkali metal salt impurities introduced with the epoxide carbonylation catalyst. In certain embodiments, such methods are characterized in that the epoxide carbonylation reaction zone is essentially free of halide. In certain embodiments, the methods are characterized in that the epoxide carbonylation reaction zone has a halide content less than about 200 ppm. In certain embodiments, the methods are characterized in that the epoxide carbonylation reaction zone has a halide content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm. In certain embodiments, the methods are characterized in that the epoxide carbonylation reaction zone is essentially free of alkali metal salts. In certain embodiments, the methods are characterized in that the epoxide carbonylation reaction zone has an alkali metal salt content less than about 200 ppm. In certain embodiments, the methods are characterized in that the epoxide carbonylation reaction zone has an alkali metal salt content less than about 150 ppm, less than about 100 ppm, less than about 50 ppm, less than about 40 ppm, less than about 30 ppm, less than about 20 ppm, less than about 10 ppm, less than about 5 ppm, less than about 2 ppm, or less than about 1 ppm.

In certain embodiments of methods for providing carbonylation catalysts to an epoxide carbonylation reaction, a neutral metal carbonyl compound provided in the second catalyst feed stream has the general formula $Q'_d M_e(CO)_{w'}$, where each of Q', M, d, e, and w' is as defined above and in the classes and subclasses herein. In certain embodiments, the neutral metal carbonyl provided in the second catalyst feed stream has the general formula $Q'M(CO)_{w'}$. In certain embodiments, a neutral metal carbonyl provided in the second catalyst feed stream has the general formula $M(CO)_{w'}$. In certain embodiments, a neutral metal carbonyl provided in the second catalyst feed stream has the general formula $Q'M_2(CO)_{w'}$. In certain embodiments, a neutral metal carbonyl provided in the second catalyst feed stream has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$.

In certain embodiments, a neutral metal carbonyl compound provided in the second catalyst feed stream comprises a cobalt carbonyl compound. In certain embodiments, a neutral metal carbonyl compound provided in the second catalyst feed stream is $Co_2(CO)_8$. In certain embodiments, a neutral metal carbonyl compound provided in the second catalyst feed stream is $Co_4(CO)_{12}$. In certain embodiments, a neutral metal carbonyl compound provided in the second catalyst feed stream is a mixture of two or more cobalt carbonyl species.

In certain embodiments, the rate of addition of the first feed stream and the rate of addition of the second feed stream are controlled to provide a particular molar ratio of compound I or I' to the neutral metal carbonyl compound. In certain embodiments, the ratio of the molar quantity of compound I or I' fed to the carbonylation reactor per unit time to the molar quantity of metal carbonyl compound fed to the carbonylation reactor per unit time is in the range of from about 0.1:1 to about 10:1. In certain embodiments, the molar ratio of compound I or I' to the neutral metal carbonyl compound fed to the carbonylation reactor per unit time is in the range of from 0.1:1 to 2:1; or from 0.5:1 to 1.5:1; or from 0.7:1 to 1.5:1; or from 0.8:1 to 1.2:1; or from 0.9:1 to 1.1:1. In certain embodiments, the molar ratio of compound I or I' to the neutral metal carbonyl compound fed to the carbonylation reactor per unit time is in the range of from 1:1 to 5:1; or from 1:1 to 4:1; or from 1:1 to 3:1; or from 1:1 to 2:1; or from 1.2:1 to 2.5:1; or from 1.4:1 to 2:1; or from 1.2:1 to 2:1; or from 1.5:1 to 2:1.

In certain embodiments, the molar ratio of compound I or I' to the neutral metal carbonyl compound fed to the carbonylation reactor per unit time is controlled in the methods herein such that the molar ratio of aluminum atoms from the provided compound I or I' to metal atoms from the provided neutral metal carbonyl compound is in the range of about 0.5:1 to about 2:1. For example, if a neutral metal carbonyl compound is dicobalt octacarbonyl, and compound I or I' is an aluminum porphyrin complex, a feed rate providing 2:1 molar ratio of compound I or I' to a neutral metal carbonyl per unit time would provide a 1:1 molar ratio of cobalt to aluminum atoms in the reaction zone. In certain embodiments, the ratio of the of aluminum atoms provided by addition of the first catalyst feed stream to metal atoms in a neutral metal carbonyl compound provided by addition the second catalyst feed stream is in the range of from 0.5:1 to about 1.5:1, or from 0.7:1 to about 1.3:1, or from 0.8:1 to about 1.2:1, or from 0.9:1 to about 1.2:1, or from 0.9:1 to about 1.1:1, or from 0.95:1 to about 1.05:1. In certain embodiments, the ratio of the of aluminum atoms provided by addition of the first catalyst feed stream to metal atoms in a neutral metal carbonyl compound provided by addition the second catalyst feed stream is in the range of from about 1:1 to about 1:2, or from about 1:1 to about 1:1.8, or from about 1:1 to about 1:1.5, or from about 1:1 to about 1:1.4, or from about 1:1 to about 1:1.3, or from about 1:1 to about 1:1.2 or from about 1:1 to about 1:1.1.

In certain embodiments, the rate of addition of the first catalyst feed stream and the rate of addition of the second catalyst feed stream are set such that within the epoxide carbonylation reaction zone, the molar ratio of metal atoms from a provided neutral metal carbonyl compound to aluminum atoms from the provided compound I or I' is maintained at a ratio of about 1:1.

In certain embodiments the present invention encompasses a method for providing carbonylation catalysts to an epoxide carbonylation reaction, the method comprising the step of feeding a carbonylation reactor comprising a reaction zone where one or more epoxides is in contact with carbon monoxide with carbonylation catalyst by providing two separate catalyst feed streams: a first catalyst feed stream containing a compound of formula I or I' (as defined above and in the classes and subclasses herein) and a second catalyst feed stream containing a neutral cobalt carbonyl compound.

In certain embodiments, the first catalyst feed stream and the second catalyst feed stream are added to the epoxide carbonylation reactor at two separate entry points. In other embodiments, the first catalyst feed stream and the second catalyst feed stream are combined at the entry to the epoxide carbonylation reactor. In certain embodiments, the first catalyst feed stream and the second catalyst feed stream are combined prior to their entry to the epoxide carbonylation reactor, for example by flowing through a mixing tee or a static mixer prior to entry to the epoxide carbonylation reactor. In certain embodiments where the first catalyst feed stream and the second catalyst feed stream are combined prior to their entry to the epoxide carbonylation reactor they are combined in the presence of carbon monoxide. In certain embodiments, provision is made for a controlled contact time of the first and second catalyst feed streams prior to their introduction to the epoxide carbonylation reactor. In certain embodiments, the controlled contact time is in the range of 0.5 seconds to 60 minutes. In certain embodiments, the controlled contact time is in the range from 0.5 seconds to 30 seconds, from 0.5 seconds to 10 seconds, from 10 seconds to 30 seconds, or from 20 seconds to 30 seconds. In certain embodiments, the controlled contact time is in the range from 30 seconds to 5 minutes, from 30 seconds to 1 minute, from 1 minute to 2 minutes, or from 2 minutes to 5 minutes. In certain embodiments, the controlled contact time is in the range from 5 minutes to 10 minutes, from 10 minutes to 20 minutes, from 15 minutes to 30 minutes, or from 30 minutes to 60 minutes. In certain embodiments, the contact time is controlled by a control loop based on an analytical measurement of the combined catalyst feed streams. Suitable analytical methods include, but are not limited to: infrared (IR) spectroscopy, ultraviolet-visible absorption (UV-vis) spectroscopy, mass spectroscopy, gas chromatography (GC), liquid chromatography, and combinations of two or more of these. In certain embodiments, the analytical method measures one or more of: disappearance of the neutral metal carbonyl compound, disappearance of the aluminum precursor (e.g. I or I'), formation of the desired catalyst, formation of a ketone (e.g. $R^qCOR^q$), or combinations of two or more of these.

For any of the methods above, the epoxide present in the epoxide carbonylation reactor may be ethylene oxide, or any substituted epoxide. In certain embodiments, the epoxide present in the epoxide carbonylation reactor has a formula:

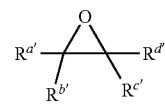

wherein:
R$^{a'}$ is hydrogen or an optionally substituted group selected from the group consisting of C$_{1-30}$ aliphatic; C$_{1-30}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-3 heteroatoms independently selected from the group consisting of nitrogen, oxygen, and sulfur;

each of R$^{b'}$, R$^{c'}$, and R$^{d'}$ is independently hydrogen or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-3 heteroatoms independently selected from the group consisting of nitrogen, oxygen, and sulfur;

wherein any of (R$^{b'}$ and R$^{c'}$), (R$^{c'}$ and R$^{d'}$), and (R$^{a'}$ and R$^{b'}$) can be taken together with their intervening atoms to form one or more rings selected from the group consisting of: optionally substituted C$_3$-C$_{14}$ carbocycle, optionally substituted C$_3$-C$_{14}$ heterocycle, optionally substituted C$_6$-C$_{10}$ aryl, and optionally substituted C$_5$-C$_{10}$ heteroaryl.

In certain embodiments, an epoxide present in the epoxide carbonylation reactor is selected from the group consisting of: ethylene oxide, propylene oxide, 1,2 butylene oxide, 2,3 butylene oxide, epoxides of higher alpha olefins, epichlorohydrin, glycidyl ethers, cyclohexene oxide, cyclopentene oxide, 3-vinyl cyclohexene oxide, 3-ethyl cyclohexene oxide, and diepoxides.

In certain embodiments, an epoxide present in the epoxide carbonylation reactor may comprise a mixture of any two or more of the above epoxides. (Thus, when an epoxide "comprises", e.g., ethylene oxide, it is understood that the provided epoxide can be ethylene oxide, or ethylene oxide in combination with one or more epoxides.)

In certain embodiments, the provided epoxide consists of ethylene oxide.

In certain embodiments, a provided epoxide consists of propylene oxide. In certain embodiments, the provided propylene oxide is enantioenriched.

In certain embodiments, epoxide carbonylation reactions in the methods above are characterized in that a product of the epoxide carbonylation is selected from the group consisting of: beta lactone, cyclic anhydride, 3-hydroxy carboxylic acid or an ester thereof, or a polyester formed by alternating copolymerization of the epoxide and carbon monoxide.

In certain embodiments, the epoxide carbonylation reactions in the methods above are characterized in that a product of the epoxide carbonylation is a beta propiolactone derivative:

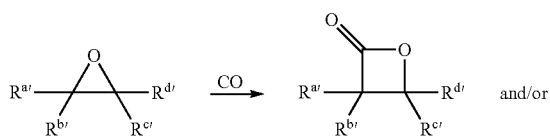

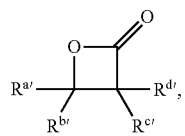

where each R$^{a'}$, R$^{b'}$, R$^{c'}$, and R$^{d'}$ is as defined above and in the classes and subclasses herein.

In certain embodiments, the epoxide carbonylation reactions in the methods above are characterized in that a product of the epoxide carbonylation is a succinic anhydride derivative:

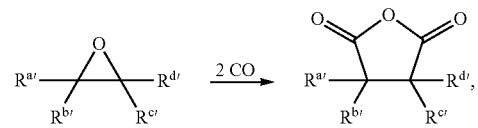

where each R$^{a'}$, R$^{b'}$, R$^{c'}$, and R$^{d'}$ is as defined above and in the classes and subclasses herein.

In certain embodiments, the epoxide carbonylation reactions in the methods above are characterized in that a product of the epoxide carbonylation is a 3-hydroxy propionic acid derivative:

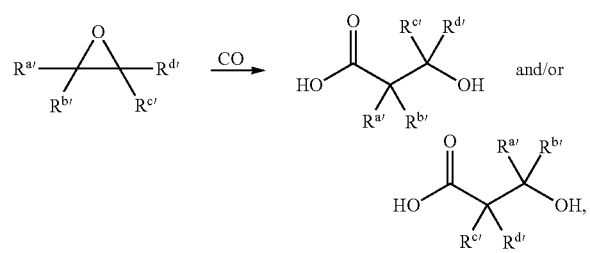

where each R$^{a'}$, R$^{b'}$, R$^{c'}$, and R$^{d'}$ is as defined above and in the classes and subclasses herein.

In certain embodiments, the epoxide carbonylation reactions in the methods above are characterized in that a product of the epoxide carbonylation is an ester of a 3-hydroxy propionic acid derivative:

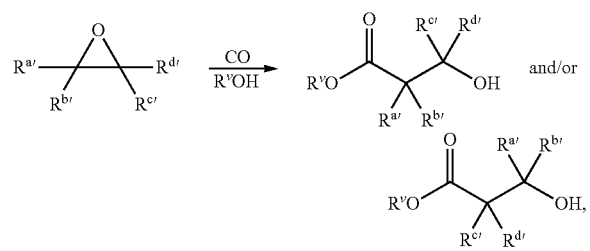

where each R$^{a'}$, R$^{b'}$, R$^{c'}$, and R$^{d'}$ is as defined above and in the classes and subclasses herein, and R$^v$ is selected from the group consisting of optionally substituted C$_{1-12}$ aliphatic and optionally substituted aryl, or R$^v$ is selected from the group consisting of methyl, ethyl, n-propyl, isopropyl, n-butyl, i-butyl, s-butyl, t-butyl, and 2-ethylhexyl, or R$^v$ is selected from the group consisting of methyl, ethyl, n-butyl, and 2-ethylhexyl.

In certain embodiments, the epoxide carbonylation reactions in the methods above are characterized in that a product of the epoxide carbonylation is a poly-3-hydroxy propionic acid derivative:

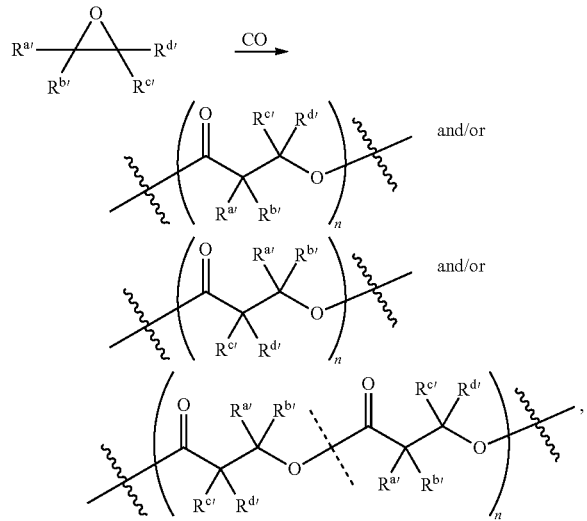

where each $R^{a'}$, $R^{b'}$, $R^{c'}$, and $R^{d'}$ is as defined above and in the classes and subclasses herein.

In certain embodiments, the epoxide is ethylene oxide and the product of the epoxide carbonylation reaction comprises beta propiolactone. In certain embodiments, the epoxide is ethylene oxide and the product of the epoxide carbonylation reaction comprises succinic anhydride. In certain embodiments, the epoxide is ethylene oxide and the product of the epoxide carbonylation reaction comprises 3-hydroxy propionic acid. In certain embodiments, the epoxide is ethylene oxide and the product of the epoxide carbonylation reaction comprises the methyl-, ethyl-, propyl-, butyl-, or 2-ethylhexyl ester of 3-hydroxy propionic acid. In certain embodiments, the epoxide is ethylene oxide and the product of the epoxide carbonylation reaction comprises polypropiolactone.

In certain embodiments, the epoxide is propylene oxide and the product of the epoxide carbonylation reaction comprises beta butyrolactone. In certain embodiments, the epoxide is propylene oxide and the product of the epoxide carbonylation reaction comprises methyl succinic anhydride. In certain embodiments, the epoxide is propylene oxide and the product of the epoxide carbonylation reaction comprises 3-hydroxy butyric acid. In certain embodiments, the epoxide is propylene oxide and the product of the epoxide carbonylation reaction comprises poly-3-hydroxy butyrate (PHB).

In certain embodiments, the methods above are adapted to feed a carbonylation reactor where the substrate is other than an epoxide. Such non-epoxide substrates include beta lactones, aziridines, and oxetanes. In certain embodiments, the methods above are adapted to feed a continuous carbonylation reactor where beta propiolactone is carbonylated to provide succinic anhydride.

IV. Detailed Description of the Aluminum Complex

In the methods and compositions described above, various aluminum complexes are described and depicted as an aluminum atom coordinated to four Q groups, for example in formulae I and I' and

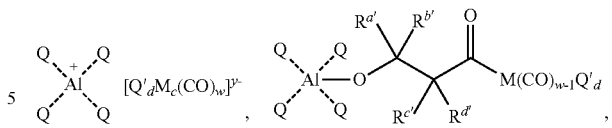

etc. this section describes these compounds in greater detail.

In certain embodiments, the four Q groups associated with the aluminum atom in the compounds herein are part of a single tetradentate ligand. In certain embodiments, the four Q groups are part of two or more separate ligands, for example, a combination of two bidendate ligands (which may be the same or different), or a combination of a tridentate ligand and a monodentate ligand. In certain embodiments, all four Q groups comprise nitrogen atoms. In certain embodiments, the Q groups comprise nitrogen and oxygen atoms (for example two N and two O, three N and one O, or three O and one N). In certain embodiments, all four Q groups comprise oxygen atoms.

In embodiments where the four Q groups associated with the aluminum atom are part of a single tetradentate ligand, the tetradentate ligand is selected from the group consisting of: porphyrin derivatives 1, salen derivatives 2, dibenzotetramethyltetraaza[14]annulene (tmtaa) derivatives 3, phthalocyaninate derivatives 4, derivatives of the Trost ligand 5, and tetraphenylporphyrin derivatives 6, as depicted below. In certain embodiments, the multidentate ligand is a salon derivative. In other embodiments, the multidentate ligand is a tetraphenylporphyrin derivative.

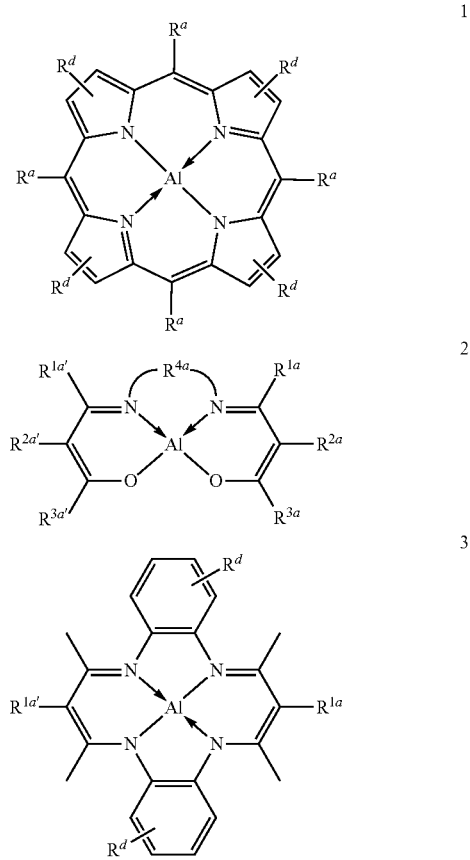

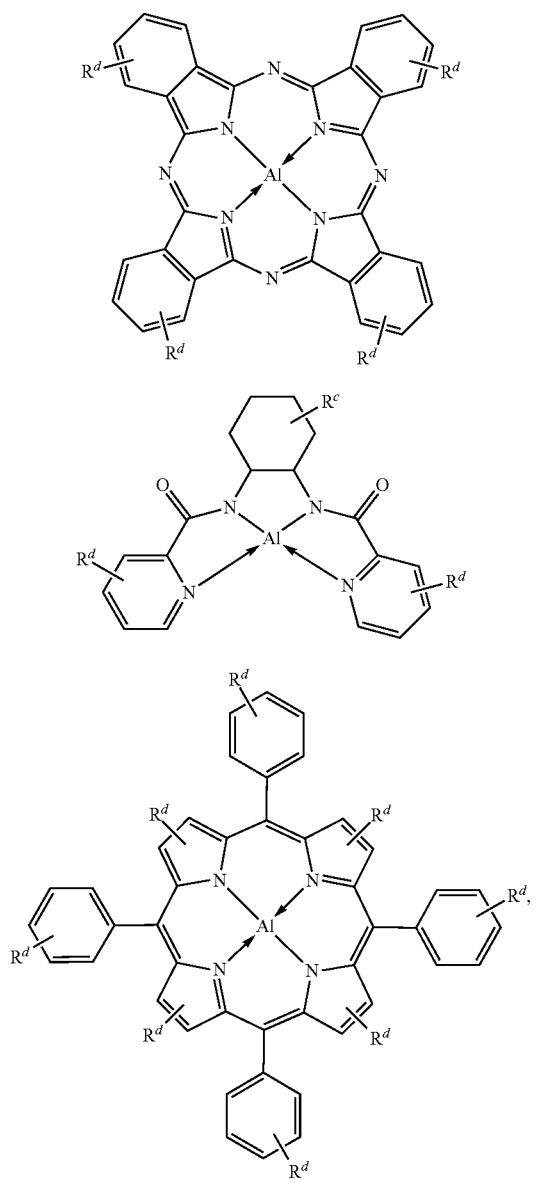

where
- $R^c$ is independently at each occurrence hydrogen, halogen, —OR, —NR$^y_2$, —SR$^y$, —CN, —NO$_2$, —SO$_2$R$^y$, —SOR$^y$, —SO$_2$NR$^y_2$; —CNO, —NRSO$_2$R$^y$, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur;
- $R^d$ is independently at each occurrence hydrogen, halogen, —OR$^4$, —NR$^y_2$, —SR, —CN, —NO$_2$, —SO$_2$R$^y$, —SOR$^y$, —SO$_2$NR$^y_2$; —CNO, —NRSO$_2$R, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where
  two or more R$^d$ groups may be taken together to form one or more optionally substituted rings,
- each R$^y$ is independently hydrogen, or an optionally substituted group selected the group consisting of: acyl; carbamoyl, arylalkyl; 6- to 10-membered aryl; C$_{1-12}$ aliphatic; C$_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two R$^y$ on the same nitrogen atom may be taken with the nitrogen atom to form an optionally substituted 4- to 7-membered heterocyclic ring having 0-2 additional heteroatoms independently selected from the group consisting of nitrogen, oxygen, and sulfur,
- R$^4$ is a hydroxyl protecting group or R$^y$, and
- R is independently at each occurrence optionally substituted C$_{1-12}$ aliphatic or optionally substituted aryl;
- R$^{1a}$, R$^{1a'}$, R$^{2a}$, R$^{2a'}$, R$^{3a}$, and R$^{3a'}$ are independently hydrogen, halogen, —OR$^4$, —NR$^y_2$, —SR$^y$, —CN, —NO$_2$, —SO$_2$R$^y$, —SOR, —SO$_2$NR$^y_2$; —CNO, —NRSO$_2$R$^y$, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where
  any of (R$^{2a'}$ and R$^{3a'}$), (R$^{2a}$ and R$^{3a}$), (R$^{1a}$ and R$^{2a}$), and (R$^{1a'}$ and R$^{2a'}$) may optionally be taken together with the carbon atoms to which they are attached to form one or more rings which may in turn be substituted with one or more R$^d$ groups; and
- R$^{4a}$ is selected from the group consisting of:

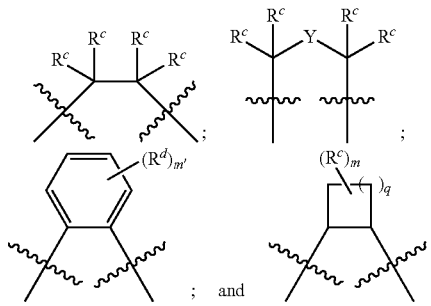

where,
- two or more $R^c$ groups may be taken together with the carbon atoms to which they are attached and any intervening atoms to form one or more rings,
- when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine, and
- Y is a divalent linker selected from the group consisting of: —[C($R^c$)$_2$]$_q$—, —N$R^y$—, —N(R)C(O)—, —C(O)N$R^y$—, —O—, —C(O)—, —OC(O)—, —C(O)O—, —S—, —SO—, —SO$_2$—, —C(=S)—, —C(=N$R^y$)—, —N=N—; a polyether; a $C_3$ to $C_8$ substituted or unsubstituted carbocycle; and a $C_1$ to $C_8$ substituted or unsubstituted heterocycle;

m is 0 or an integer from 1 to 6, inclusive;

m' is 0 or an integer from 1 to 4, inclusive;

q is 0 or an integer from 1 to 4, inclusive; and x is 0, 1, or 2.

In certain embodiments, the moiety

in the methods and compounds above comprises an aluminum-porphinato complex.

In certain embodiments, the aluminum-porphinato complex has a structure:

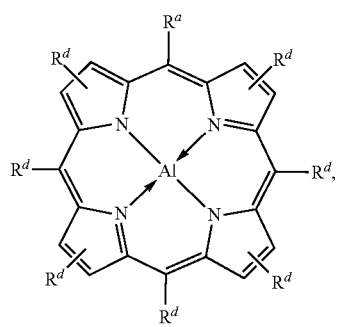

where each $R^d$ is independently as defined above and in the classes and subclasses herein.

In certain embodiments, the aluminum-porphinato complex has a structure selected from the group consisting of:

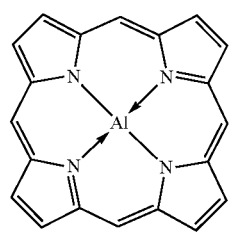

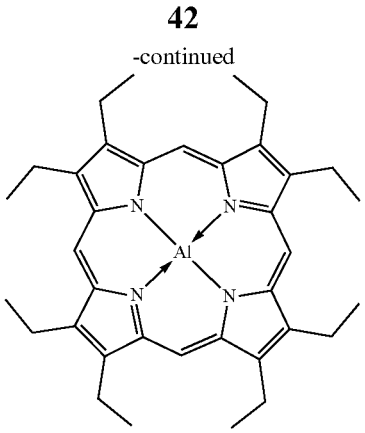

In certain embodiments, the aluminum-porphinato complex has the structure:

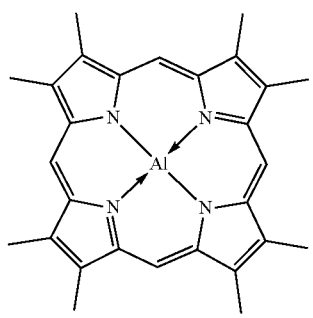

where each $R^d$ is independently as defined above and in the classes and subclasses herein.

In certain embodiments, the aluminum-porphinato complex has the structure:
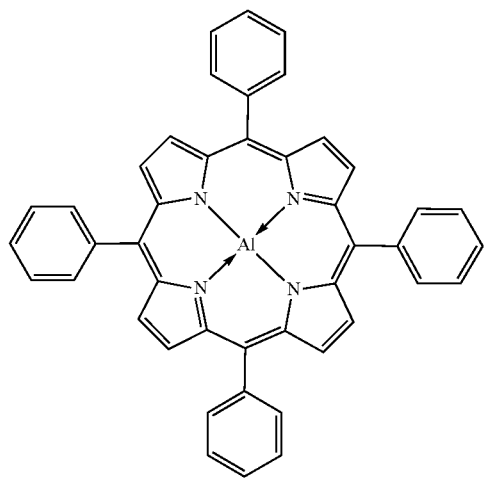
In certain embodiments, the aluminum-porphinato complex has a structure selected from the group consisting of:
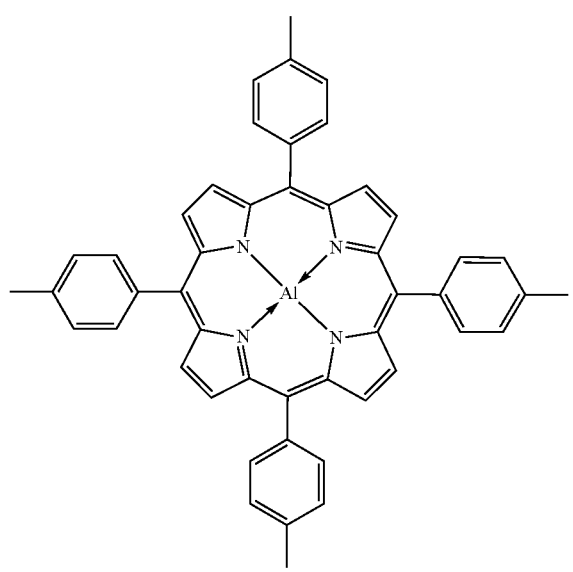
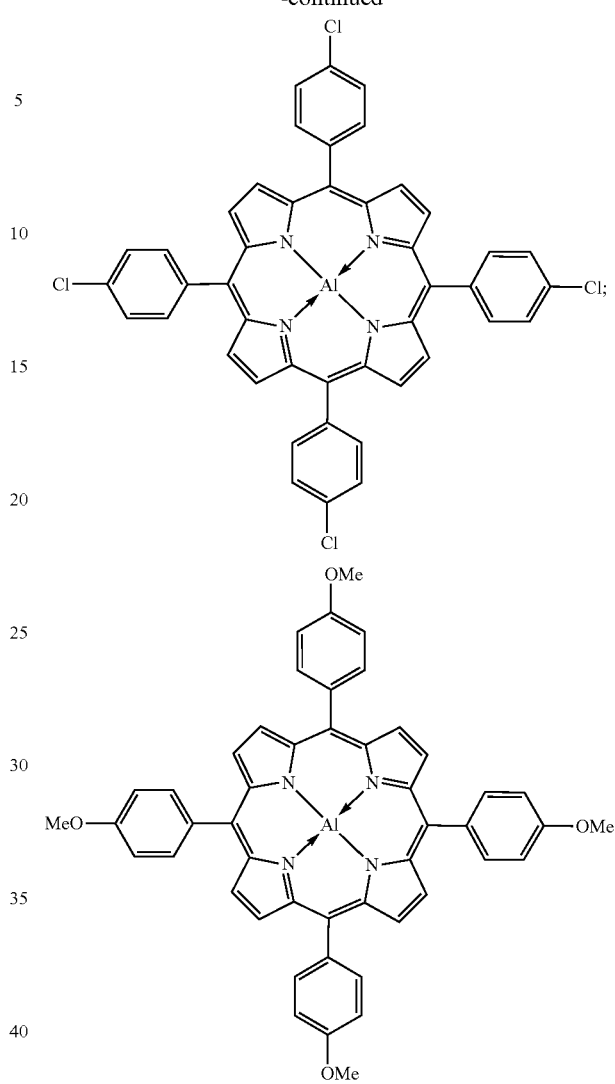
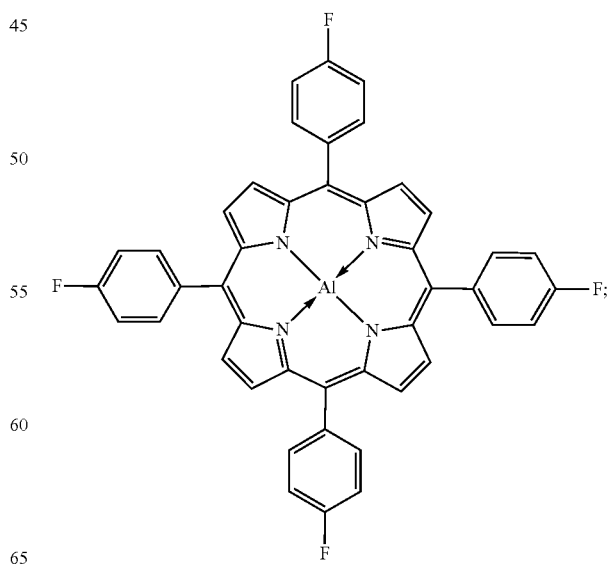

-continued

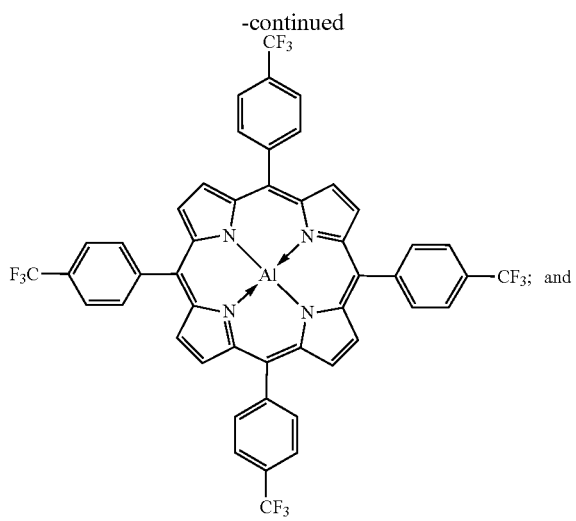

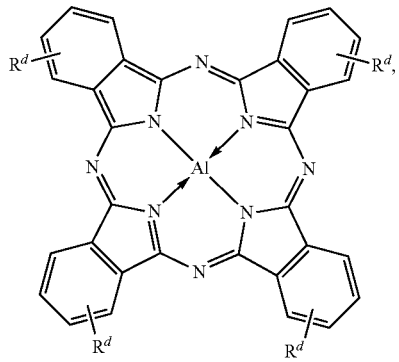

where $R^d$ is independently at each occurrence as defined above and in the classes and subclasses herein.

In certain embodiments, the moiety

in the compounds and methods above comprises an aluminum-salen complex.

In certain embodiments, the moiety

in the compounds and methods described herein has a structure:

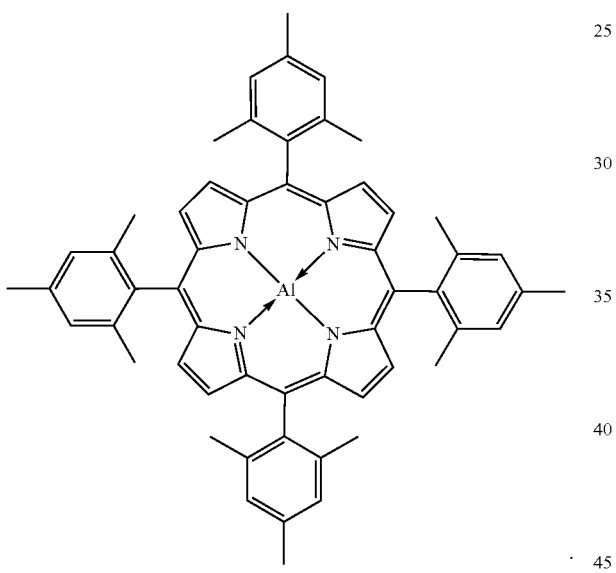

In certain embodiments, the moiety

in the compounds and methods above comprises an aluminum-phthalocyanine complex.

In certain embodiments, the moiety

in the compounds and methods described herein has a structure:

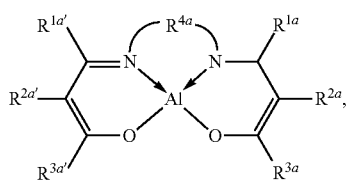

where each of $R^{1a}$, $R^{1a'}$, $R^{2a}$, $R^{2a'}$, $R^{3a}$, $R^{3a'}$ and $R^{4a}$, is as defined above and in the classes and subclasses herein.

In certain embodiments, the moiety

in the compounds and methods described herein has the structure Ia:

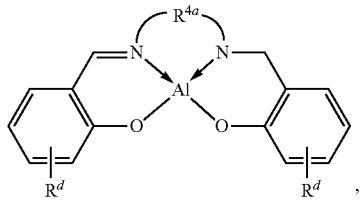

where each $R^d$ and $R^{4a}$ is independently as defined above and in the classes and subclasses herein.

In certain embodiments, the moiety

in the compounds and methods described herein has the structure:

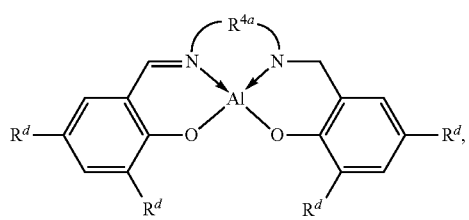

where each $R^d$ and $R^{4a}$ is independently as defined above and in the classes and subclasses herein.

In certain embodiments, the moiety

in the compounds and methods described herein has the structure:

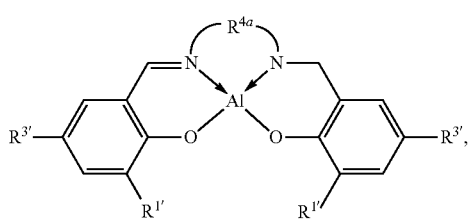

where $R^{4a}$ is as defined above and in the classes and subclasses herein, and
$R^{1'}$ and $R^{3'}$ are, independently at each occurrence, selected from the group consisting of: hydrogen, halogen, optionally substituted $C_{1-20}$ aliphatic, optionally substituted aryl, and $OR^y$, where $R^y$ is as defined above.

In certain embodiments, $R^{1'}$ and $R^{3'}$ are, independently at each occurrence, selected from the group consisting of: hydrogen, optionally substituted $C_{1-12}$ aliphatic and optionally substituted aryl. In certain embodiments, at least one occurrence of $R^{1'}$ or $R^{3'}$ is hydrogen. In certain embodiments, at least one occurrence of $R^{1'}$ or $R^{3'}$ is $C_{1-6}$ aliphatic. In certain embodiments, at least one occurrence of $R^{1'}$ or $R^{3'}$ is substituted $C_{1-6}$ aliphatic. In certain embodiments, at least one occurrence of $R^{1'}$ or $R^{3'}$ is optionally substituted aryl.

In certain embodiments, the moiety

in the compounds and methods described herein has the structure:

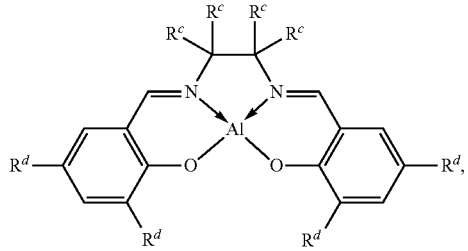

where each $R^c$ and $R^d$ is independently as defined above and in the classes and subclasses herein.

In certain embodiments, the moiety

in the compounds and methods described herein has the structure:

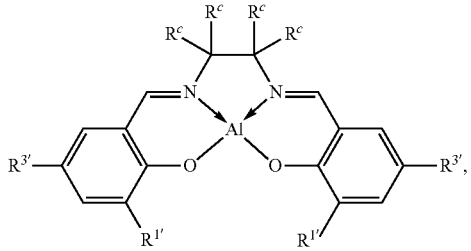

where each $R^c$, $R^{1'}$, and $R^{3'}$ is independently as defined above and in the classes and subclasses herein.

In certain embodiments, the moiety

in the compounds and methods described herein has the structure:
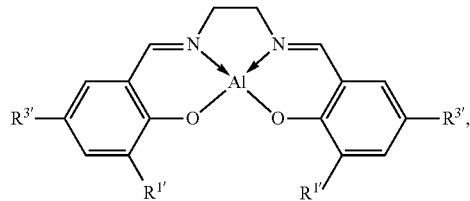
where each $R^{1'}$, and $R^{3'}$ is independently as defined above and in the classes and subclasses herein.
In certain embodiments, the moiety
in the compounds and methods described herein is selected from the group consisting of:
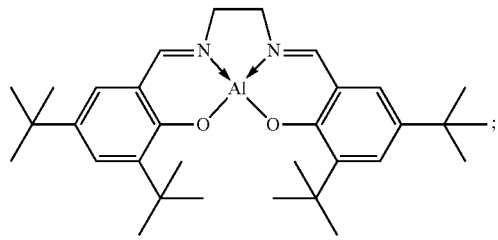
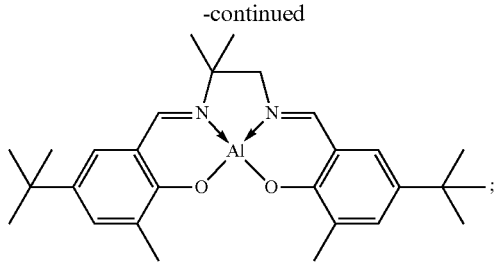
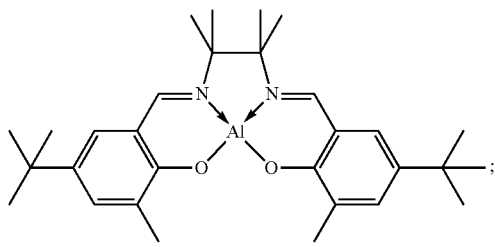
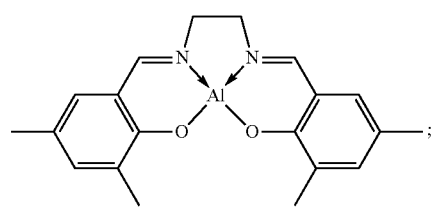
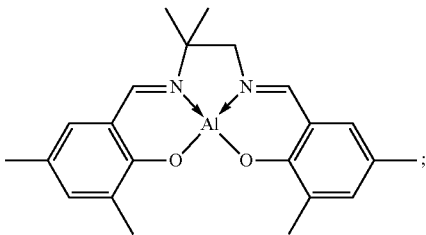
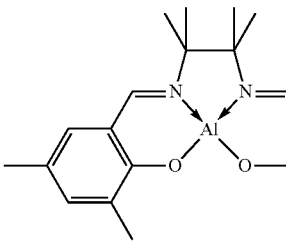
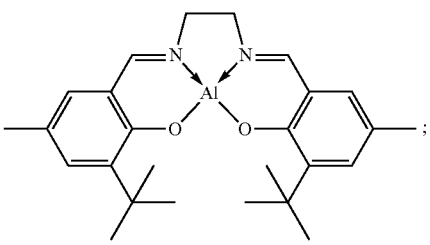
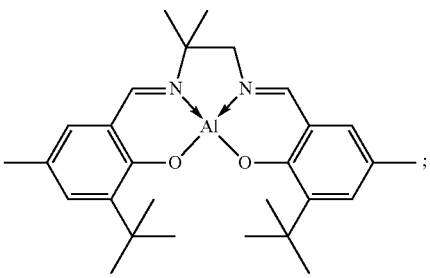

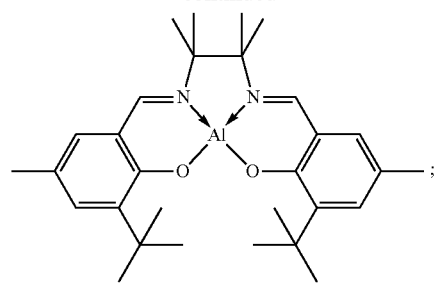
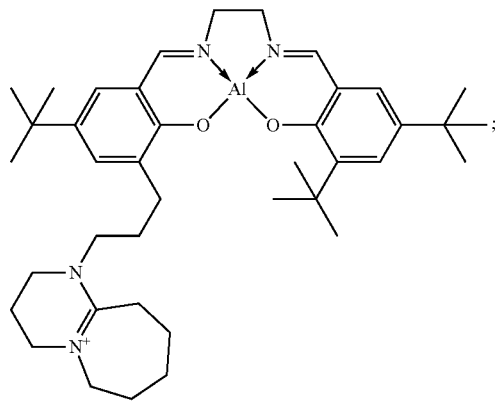
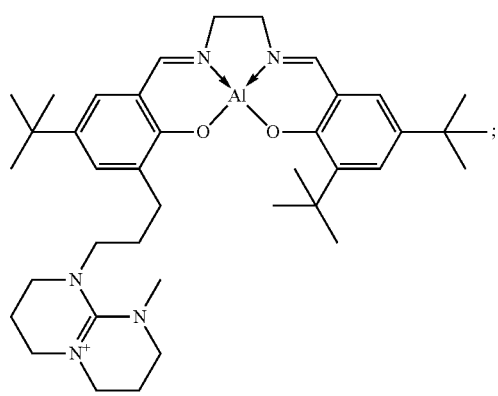
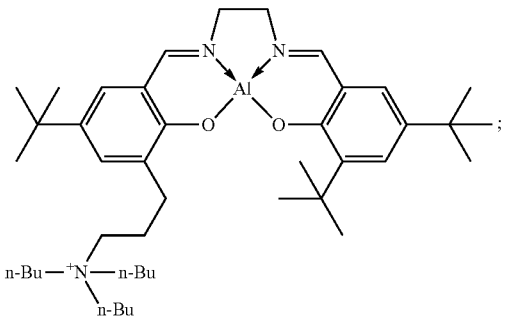
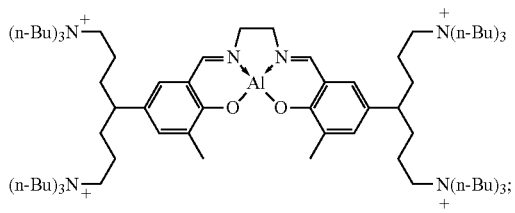
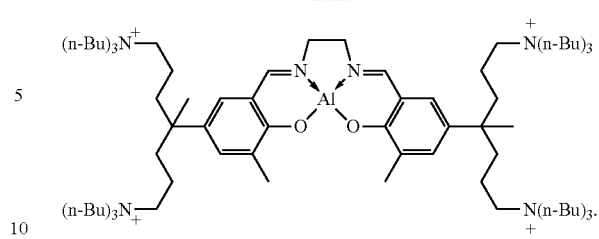
In certain embodiments, the moiety
in the compounds and methods described herein has the structure:
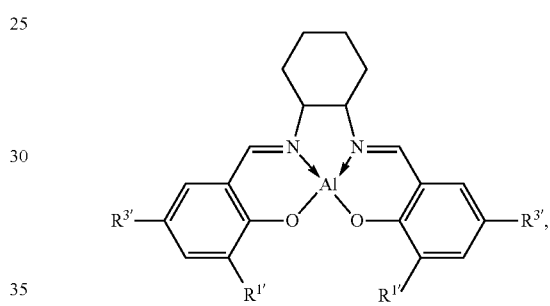
where each $R^{1'}$ and $R^{3'}$ is independently as defined above and in the classes and subclasses herein.
In certain embodiments, the moiety
in the compounds and methods described herein is selected from the group consisting of:
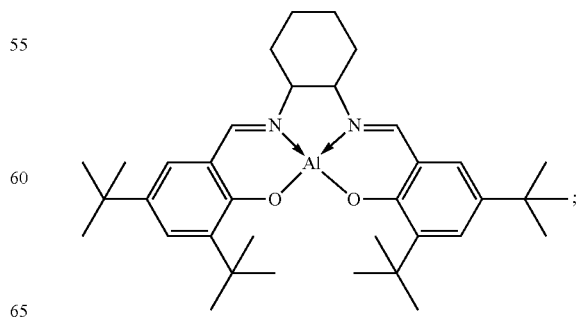

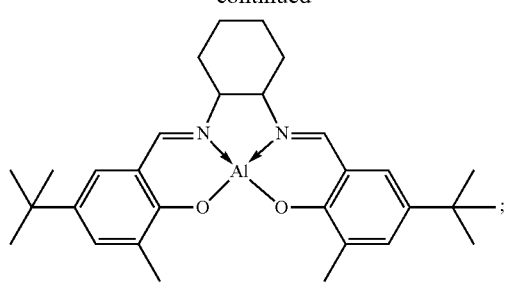
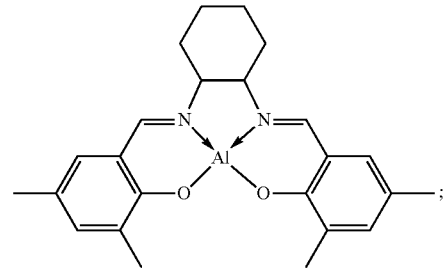
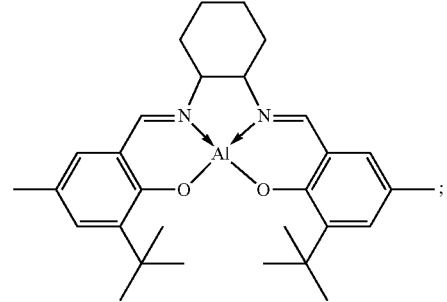
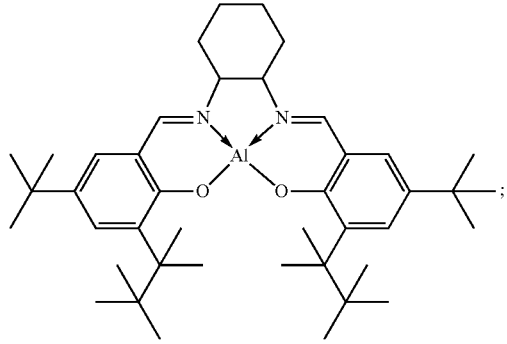
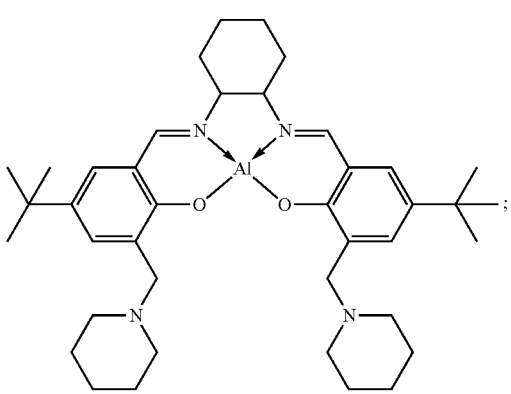
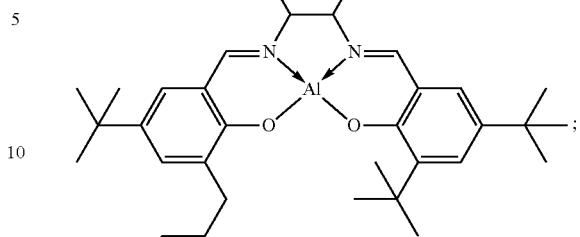
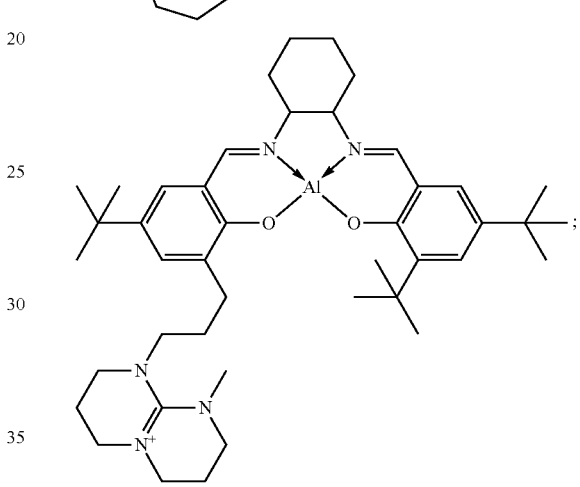
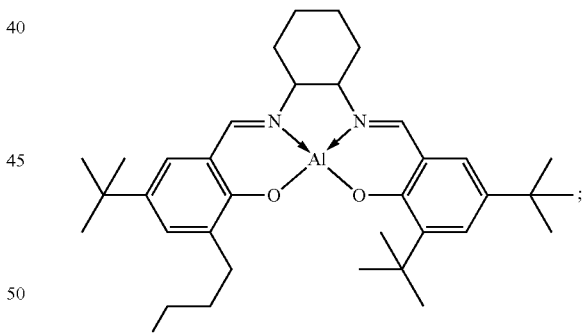
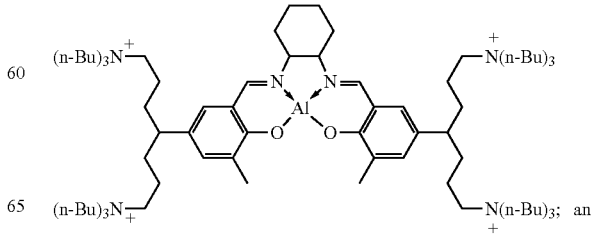

-continued

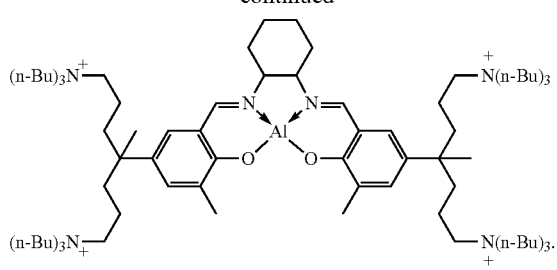

In certain embodiments, the moiety

in the compounds and methods described herein has the structure:

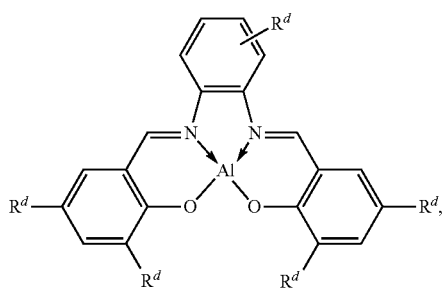

where each $R^d$ is independently as defined above in the classes and subclasses herein.

In certain embodiments, the moiety

in the compounds and methods described herein has the structure:

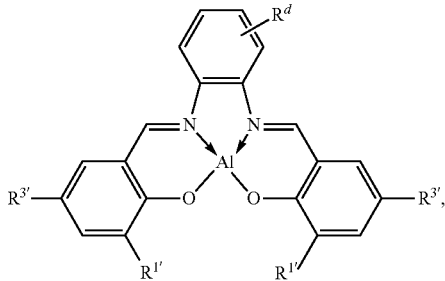

where each $R^d$, $R^{1'}$, and $R^{3'}$ is independently as defined above and in the classes and subclasses herein.

In certain embodiments, the moiety

in the compounds and methods described herein is selected from the group consisting of:

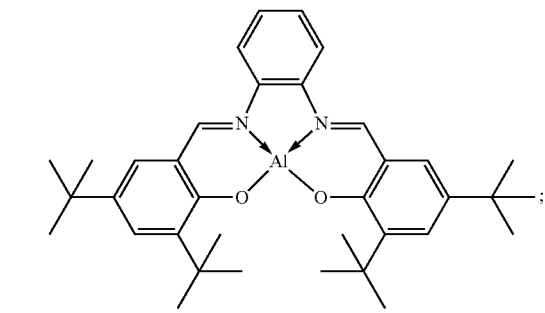

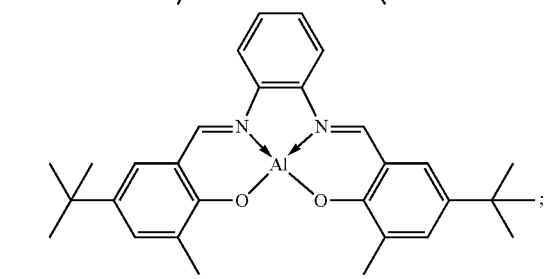

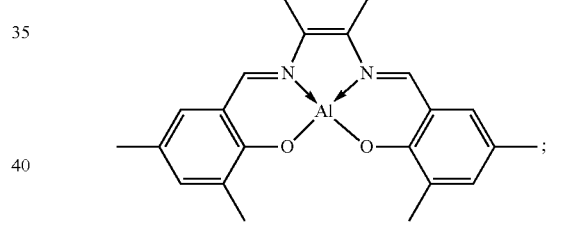

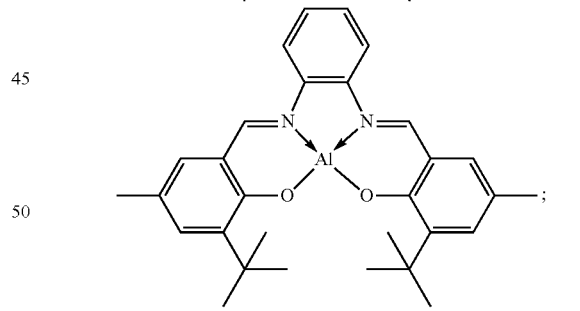

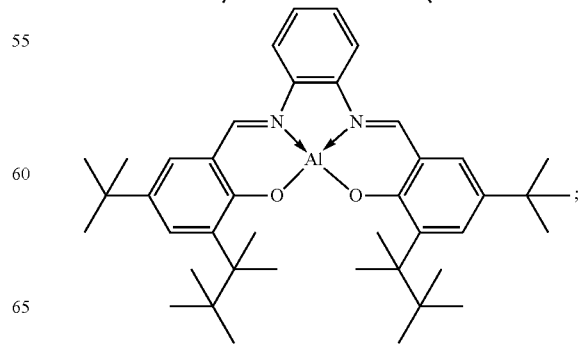

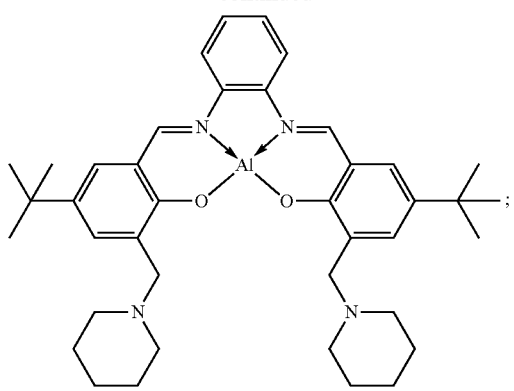

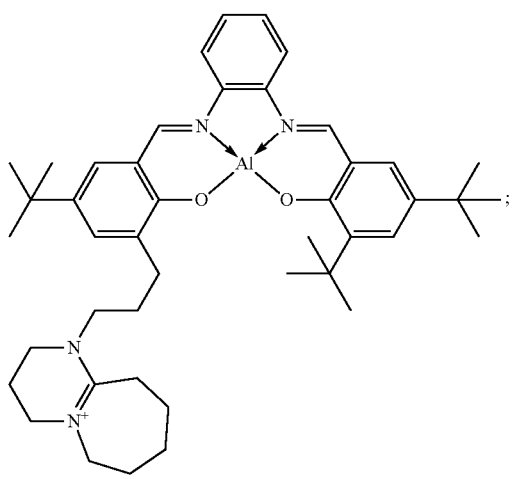

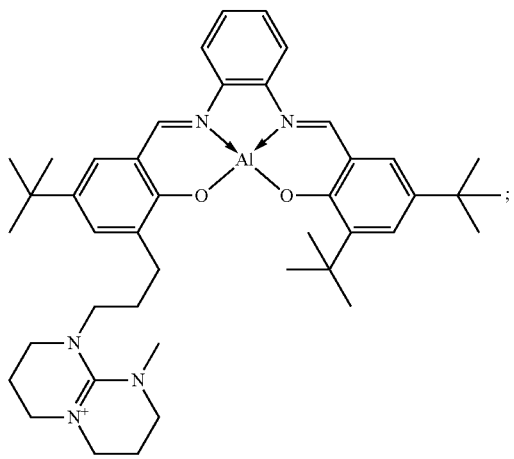

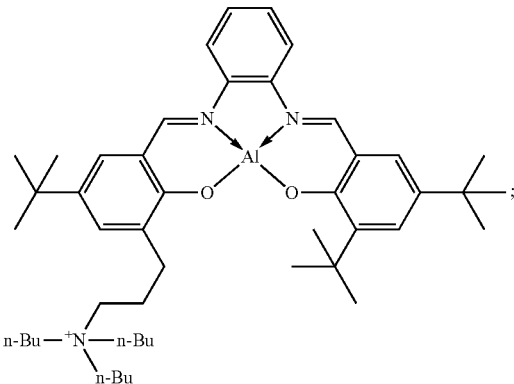

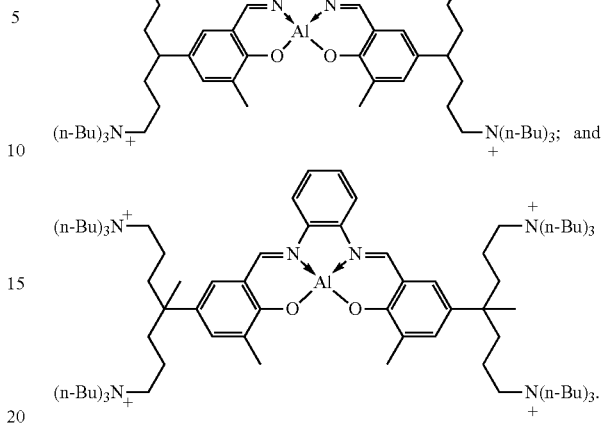

In certain embodiments, the moiety

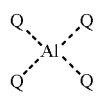

in the compounds and methods described herein comprises an aluminum-tmtaa complex.

In certain embodiments, the moiety

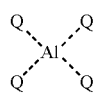

in the compounds and methods described herein has the structure:

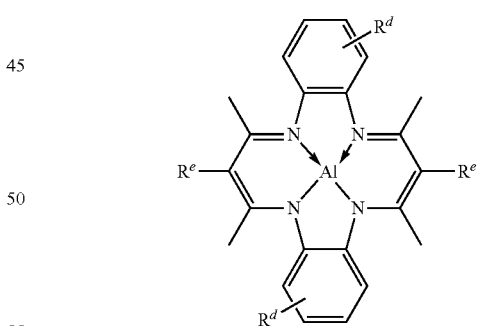

where $R^d$ is independently at each occurrence as defined above and in the classes and subclasses herein, and $R^e$ at each occurrence is independently hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur.

In certain embodiments, the moiety

in the compounds and methods described herein has the structure:

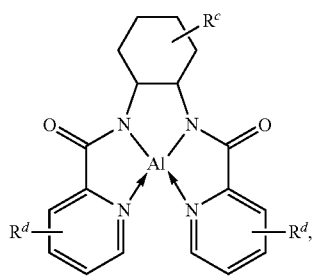

where each of $R^c$ and $R^d$ is as defined above and in the classes and subclasses herein.

In certain embodiments, for any of the aluminum complexes above having one or more $R^d$ groups, each occurrence of $R^d$ is independently selected from the group consisting of: hydrogen, halogen, optionally substituted $C_{1-6}$ aliphatic, or optionally substituted aryl. In certain embodiments, each $R^d$ is hydrogen, optionally substituted $C_{1-6}$ aliphatic, or optionally substituted aryl. In some embodiments, each $R^d$ is hydrogen. In certain embodiments, at least one $R^d$ is optionally substituted $C_{1-6}$ aliphatic. In certain embodiments, at least one $R^d$ is optionally substituted $C_{1-4}$ aliphatic. In some embodiments, at least one $R^d$ is optionally substituted aryl. In some embodiments, $R^d$ is substituted phenyl. In some embodiments, at least one $R^d$ is unsubstituted phenyl. In some embodiments, at least one $R^d$ is phenyl substituted with one or more substituents selected from the group consisting of halogen, —$NO_2$, —CN, $C_{1-6}$ aliphatic optionally substituted with one or more halogens, and —$OC_{1-6}$ aliphatic.

In certain embodiments, for any of the aluminum complexes above having one or more $R^c$ groups, each occurrence of $R^c$ is independently selected from the group consisting of: hydrogen, halogen, optionally substituted $C_{1-6}$ aliphatic and optionally substituted aryl. In some embodiments, each $R^2$ is hydrogen, halogen, or optionally substituted $C_{1-6}$ aliphatic. In some embodiments, each $R^2$ is hydrogen. In some embodiments, $R^2$ is optionally substituted $C_{1-6}$ aliphatic. In some embodiments, $R^2$ is ethyl. In some embodiments, $R^2$ is methyl.

The compounds of formula I in the methods herein have a carbon substituent bonded to the aluminum atom denoted $R^q$. As described above, $R^q$ is an optionally substituted aliphatic group or aryl group. In certain embodiments, $R^q$ is a $C_{1-20}$ aliphatic group. In certain embodiments, $R^q$ is a $C_{1-12}$ aliphatic group. In certain embodiments, $R^q$ is a Cp-s aliphatic group. In certain embodiments, $R^q$ is a $C_{1-6}$ aliphatic group. In certain embodiments, $R^q$ is a $C_{1-4}$ aliphatic group.

In certain embodiments, $R^q$ is selected from the group consisting of methyl, ethyl, n-propyl, i-propyl, n-butyl, i-butyl, and octyl. In certain embodiments, $R^q$ is ethyl. In certain embodiments, $R^q$ is methyl.

In certain embodiments, $R^q$ may correspond to an alkyl group of an available trialkyl aluminum compound. Several trialkylaluminum reagents are commercially available and processes for the preparation trialkylaluminum reagents are well known in the art: for example, by methods described in U.S. Pat. Nos. 3,006,942 and 3,960,912 (the contents of each of which are incorporated herein by reference). In some embodiments, a trialkylaluminum reagent is trimethylaluminum. In some embodiments, a trialkylaluminum reagent is triethylaluminum. In some embodiments, a trialkylaluminum reagent is tripropylaluminum. In some embodiments, a trialkylaluminum reagent is triisobutylaluminum. In some embodiments, a trialkylaluminum reagent is trioctylaluminum.

In some embodiments, compounds of formula I may be conveniently obtained by treatment of suitable protic ligands (e.g. compounds having one or more Q-H groups) with a trialkyl aluminum reagent such as those described above. This typically results in the displacement of one or more of the alkyl groups from the aluminum by Q-groups. For example, in the case where compound I is an aluminum tetraphenyl porphyrin complex, it may be obtained according to the reaction shown in Scheme 1:

Scheme 1

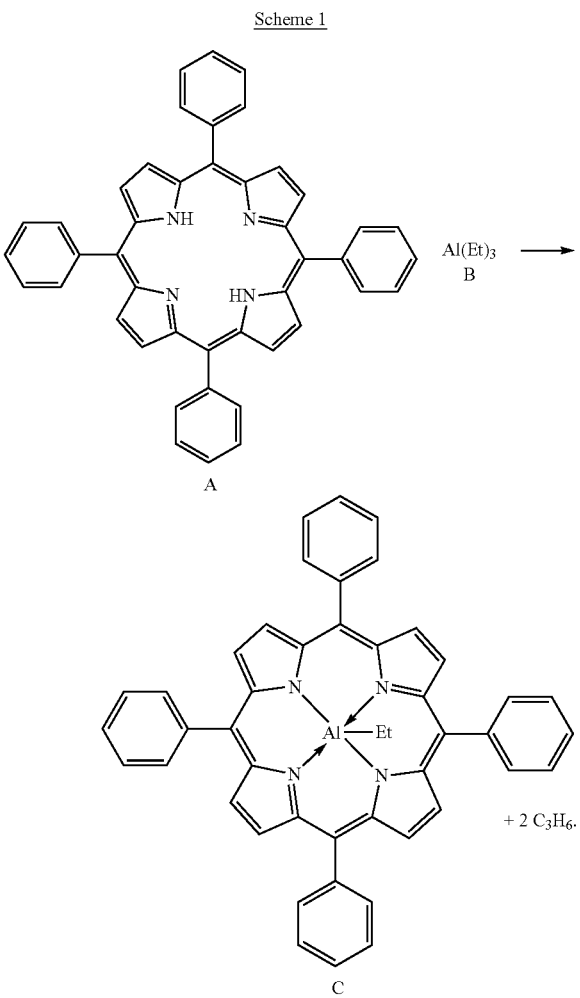

Similar means can be utilized to form other compounds of formula I by combining trialkyl aluminums with suitable protic ligands such as those described above. The skilled artisan will recognize that the reaction conditions will need to be controlled and modified to account for the reactivity of certain ligands or ligand precursors and that strategies such as controlled addition rates, lowered temperatures, selection of particular solvents and additives may be necessary to obtain the desired compounds. Such methods and conditions will constitute routine experimentation to those skilled in the art of organometallic synthesis.

V. Methods of Making Ketones

In another aspect, the present invention encompasses methods for the synthesis of symmetrical ketones.

In certain embodiments, such methods comprise the step of contacting an aluminum compound of formula I:

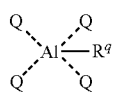

with a neutral metal carbonyl compound (as defined above and in the classes and subclasses herein) to provide a product having a formula:

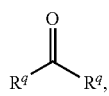

where each of Q and $R^q$ are as defined above and in the classes and subclasses herein.

In certain embodiments, compound I comprises an aluminum porphyrin complex.

In certain embodiments, $R^q$ is a $C_{1-20}$ aliphatic group. In certain embodiments, $R^q$ is a $C_{1-12}$ aliphatic group. In certain embodiments, $R^q$ is a $C_{1-8}$ aliphatic group. In certain embodiments, $R^q$ is a $C_{1-6}$ aliphatic group. In certain embodiments, $R^q$ is a $C_{1-4}$ aliphatic group.

In certain embodiments, $R^q$ is selected from the group consisting of methyl, ethyl, n-propyl, i-propyl, n-butyl, i-butyl, and octyl. In certain embodiments, $R^q$ is ethyl. In certain embodiments, $R^q$ is methyl.

In certain embodiments of the inventive methods for synthesizing ketones, the neutral metal carbonyl compound provided has the general formula $Q'_dM_e(CO)_{w'}$, where each Q', M, d, and e, is as defined above and in the classes and subclasses herein and w' is a number such as to provide a stable neutral metal carbonyl complex. In certain embodiments, the neutral metal carbonyl has the general formula $Q'M(CO)_{w'}$. In certain embodiments, the neutral metal carbonyl has the general formula $M(CO)_{w'}$. In certain embodiments, the neutral metal carbonyl has the general formula $Q'M_2(CO)_{w'}$. In certain embodiments, the neutral metal carbonyl has the general formula $M_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$. The term "such as to provide a stable neutral metal carbonyl for $Q'_dM_e(CO)_{w'}$ is used herein to mean that $Q'_dM_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments of the inventive methods for synthesizing ketones, a neutral metal carbonyl compound provided is a cobalt carbonyl compound. In certain embodiments of the inventive methods for synthesizing ketones, a neutral metal carbonyl compound provided is dicobalt octacarbonyl.

In certain embodiments of the inventive methods for synthesizing ketones, a compound of formula I and a neutral metal carbonyl compound are contacted under CO pressure. In certain embodiments, the CO pressure is in the range from about 2 atmospheres to to about 400 atmospheres. In certain embodiments, compound I and the neutral metal carbonyl compound are contacted under an atmosphere comprising CO at a pressure between about 2 atmospheres and about 100 atmospheres, or between about 5 atmosphere and about 50 atmospheres, or between about 10 atmospheres and about 20 atmospheres, or between about 20 atmospheres and about 50 atmospheres, or between about 50 atmospheres and about 100 atmospheres.

EXAMPLES

General

All synthetic experiments were done under $N_2$. THF was purified by passing through OxiClear™ column. Anhydrous hexanes was purchased from Aldrich and bubbled with $N_2$ for 2 h before use.

Example 1—Syntheses of [(TPP)Al(THF)$_2$][Co(CO)$_4$] with Aluminum Alkyls

In a 2 L flask, 60.0 g of (TPP)AlEt was dissolved in 1120 mL of THF. To the solution, 16.2 g of $Co_2(CO)_8$ containing 1-5 wt % hexanes was added. The reaction was stirred at room temperature for 16 h under 7 psig of CO. After the reaction, the reaction mixture was filtered through a frit. The filtrate was then transferred to a 5 L flask. While stirred, 2240 mL of anhydrous hexanes was added to the filtrate. The mixture was allowed to stand for 24-72 h. The resulting purple precipitate was filtered by a frit, rinsed with fresh hexanes and dried under vacuum (79.2 g). From ICP-AES and $^1$H-NMR in THF d-8, the product was confirmed to be [(TPP)Al(THF)$_2$][Co(CO)$_4$].

The same procedure as described above was used, except that 2.0 g of (TPP)AlEt, 0.9 g of $Co_4(CO)_{12}$, and 40 mL of THF were used for the reaction and the reaction was stirred for 4 days under 7 psig of CO. The reaction produced 2.6 g of a purple solid, which was confirmed to be [(TPP)Al(THF)$_2$][Co(CO)$_4$] by $^1$H NMR and ICP-AES.

Example 2—Synthesis of [(TPP)Al(THF)$_2$][Co(CO)$_4$] with Aluminum Propionate

In a 50 mL flask, 42.6 mg of (TPP)AlOC(O)CH$_2$CH$_3$, 21.7 mg of $Co_2(CO)_8$, and 10 mL of THF were added. The mixture was stirred overnight. After the reaction, the reaction was stripped of volatiles. The remaining solid was confirmed to contain [(TPP)Al(THF)$_2$][Co(CO)$_4$] by 1H NMR in THF d-8.

Example 3—Sodium Content of Aluminum Complexes

Using ICP-AES, the sodium content of the products of Examples 1 and 2 was measured and found to be below the detectable limit. In contrast, the sodium content of the same complexes prepared by salt metathesis were found to have sodium wt % in the range of 0.04 to 0.23 for 10 different preparations.

Example 4—Synthesis of Ketones

In an NMR spectrum of the reaction product resulting from treatment of (TPP)AlEt with 0.5 eq. of Co$_2$(CO)$_8$, 0.24 molar equiv. of pentanone (relative to the catalyst) was observed in the 1H NMR spectrum after the reaction. In addition, butane was detected in the volatiles from the filtrate and hexanes wash of the crystallized catalyst.

Example 5—Additional Syntheses

Using the procedures described in Examples 1 and 2, the aluminum complexes [(OEP)Al(THF)$_2$][Co(CO)$_4$] and [(McOTPP)Al(THF)$_2$][Co(CO)$_4$] can also be made by starting with the appropriate aluminum ligand (i.e., octaethylporphyrin or 5,10,15,20-tetrakis(4-methoxyphenyl)porphyrin).

Example 6—Continuous Carbonylation Processes

An exemplary embodiment for a continuous carbonylation process is depicted in FIG. 1. Carbon monoxide, epoxide, a first catalyst stream (1), and a second catalyst stream (2) as described here are fed to a carbonylation reactor 100 (e.g., a CSTR). The product stream 101 is fed to catalyst separator 100b for the removal (e.g., via nanofiltration) of carbonylation catalyst. The carbonylation product stream is withdrawn via 102, while a recycling loop R1 feeds carbonylation catalyst back to the carbonylation reactor 100.

Figure 2:
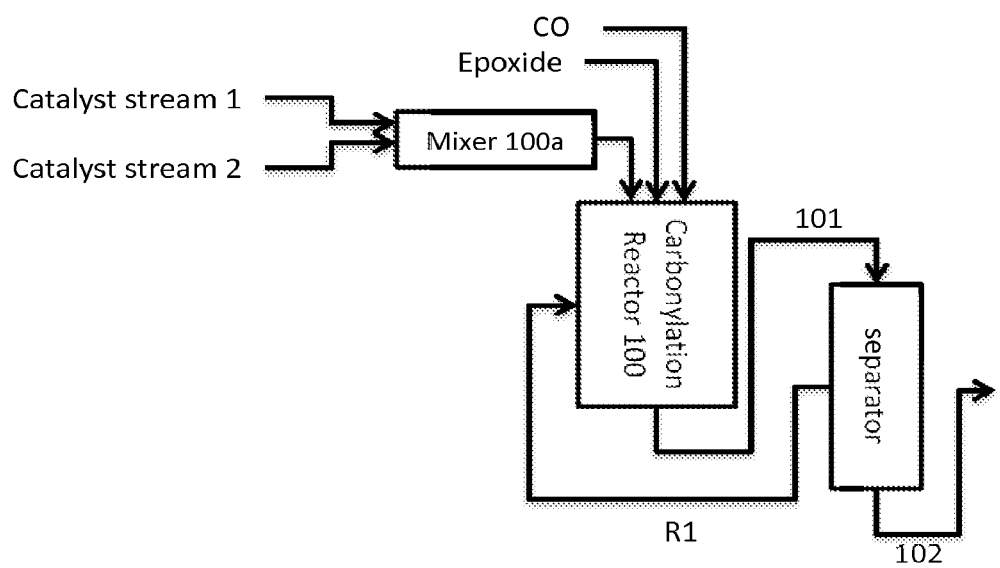
FIG. 2 shows an alternate process schematic of a disclosed continuous carbonylation method where a first catalyst feed stream and second catalyst feed stream are combined in a mixer prior to being fed to a continuous carbonylation reactor.

FIG. 2 depicts a similar embodiment with an alternative approach of pre-mixing the first catalyst stream and second catalyst stream in a mixer 100a prior to feeding into the carbonylation reactor 100.

Other Embodiments

It is to be understood that the embodiments of the invention herein described are merely illustrative of the application of the principles of the invention. Therefore, it will be appreciated that the scope of this invention is to be defined by the appended claims rather than by the specific embodiments that have been presented by way of example.

What is claimed is:

1. A method for preparing an aluminum-based carbonylation catalyst and a ketone, the method comprising reacting a compound of formula I with a neutral metal carbonyl compound to produce an aluminum-based carbonylation catalyst and a ketone, wherein:

the compound of formula I is

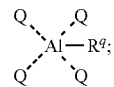

I the neutral metal carbonyl compound is Co$_2$(CO)$_8$;
the aluminum-based carbonylation catalyst is

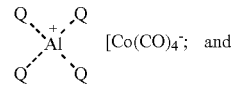

the ketone is

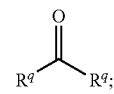

wherein:
Q is a nitrogen atom and the four Q groups are part of a single porphyrin ligand; and
R$^q$ is alkyl.

2. The method of claim 1, wherein the moiety

is:

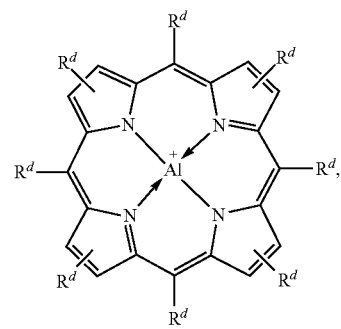

wherein:
R$^d$ is independently at each occurrence hydrogen, halogen, —OR$^4$, —NR$^y_2$, —SR, —CN, —NO$_2$, —SO$_2$R$^y$, —SOR$^y$, —SO$_2$NR$^y_2$; —CNO, —NRSO$_2$R$^y$, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where two or more R$^d$ groups may be taken together to form one or more optionally substituted rings, each R$^y$ is independently hydrogen, or an optionally substituted group selected from the group consisting of: carbamoyl, arylalkyl; 6- to 10-membered aryl; C$_{1-12}$ aliphatic; C$_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two R$^y$ on the same nitrogen atom may be taken with the nitrogen atom to form an optionally substituted 4- to 7-membered heterocyclic ring having 0-2 additional heteroatoms independently selected from the group consisting of nitrogen, oxygen, and sulfur, R$^4$ is a hydroxyl protecting group or R$^y$, and R is independently at each occurrence optionally substituted C$_{1-12}$ aliphatic or optionally substituted aryl.

3. The method of claim 1, wherein the moiety

is selected from the group consisting of:

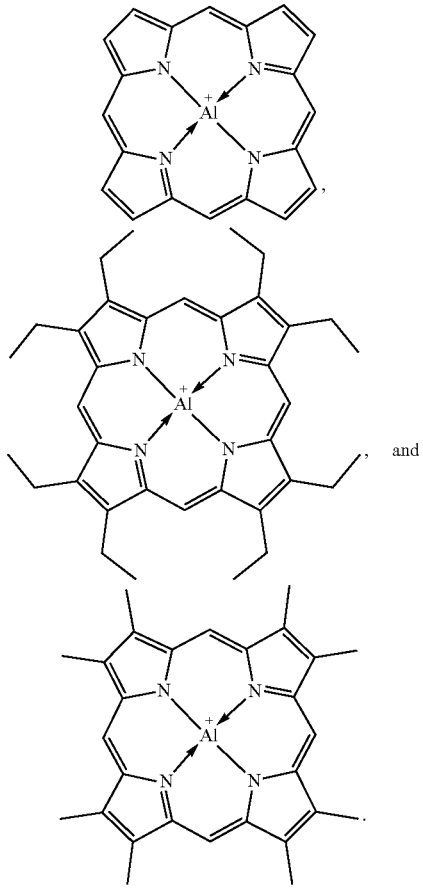

4. The method of claim 1, wherein the moiety

is:

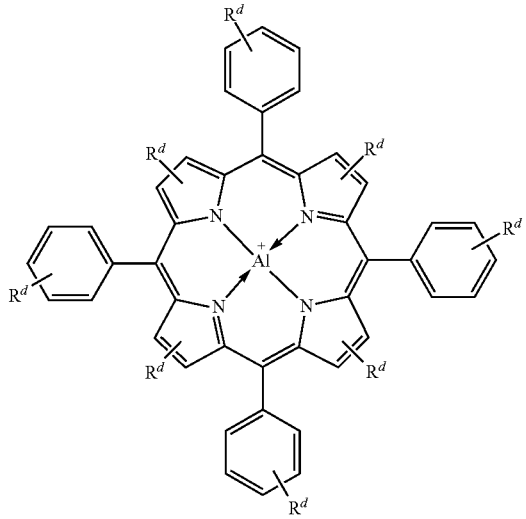

wherein:
R$^d$ is independently at each occurrence hydrogen, halogen, —OR$^4$, —NR$^y_2$, —SR, —CN, —NO$_2$, —SO$_2$R$^y$, —SOR$^y$, —SO$_2$NR$^y_2$; —CNO, —NRSO$_2$R$^y$, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where two or more R$^d$ groups may be taken together to form one or more optionally substituted rings, each R$^y$ is independently hydrogen, or an optionally substituted group selected from the group consisting of: carbamoyl, arylalkyl; 6- to 10-membered aryl; C$_{1-12}$ aliphatic; C$_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two R$^y$ on the same nitrogen atom may be taken with the nitrogen atom to form an optionally substituted 4- to 7-membered heterocyclic ring having 0-2 additional heteroatoms independently selected from the group consisting of nitrogen, oxygen, and sulfur, R$^4$ is a hydroxyl protecting group or R$^y$, and R is independently at each occurrence optionally substituted $C_{1-12}$ aliphatic or optionally substituted aryl.
5. The method of claim 1, wherein the moiety
is:
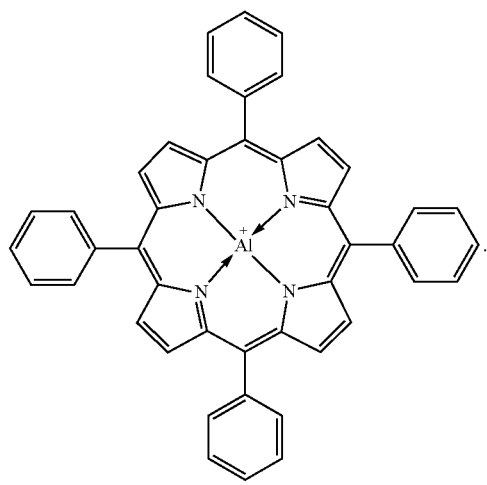
6. The method of claim 1, wherein the moiety
is selected from the group consisting of:
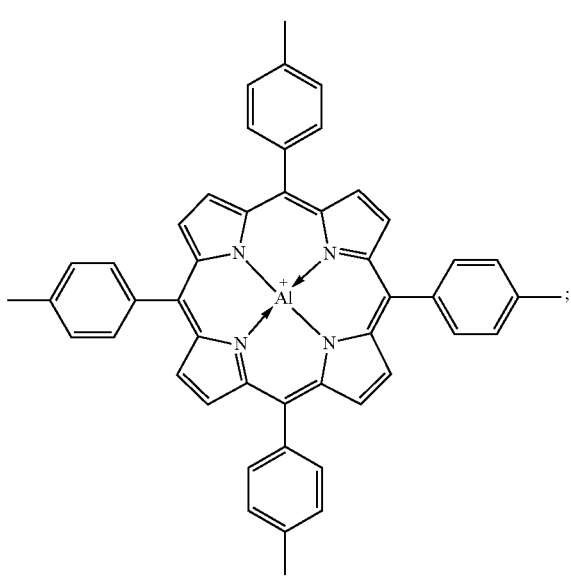
-continued
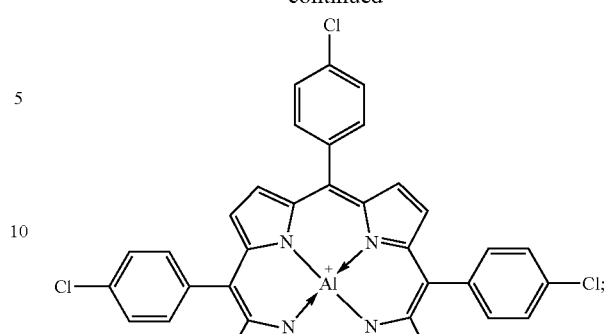
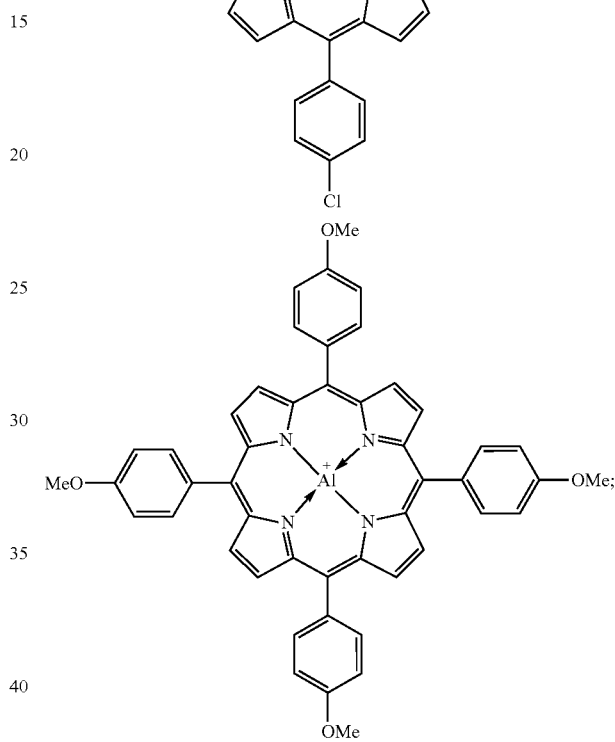

-continued

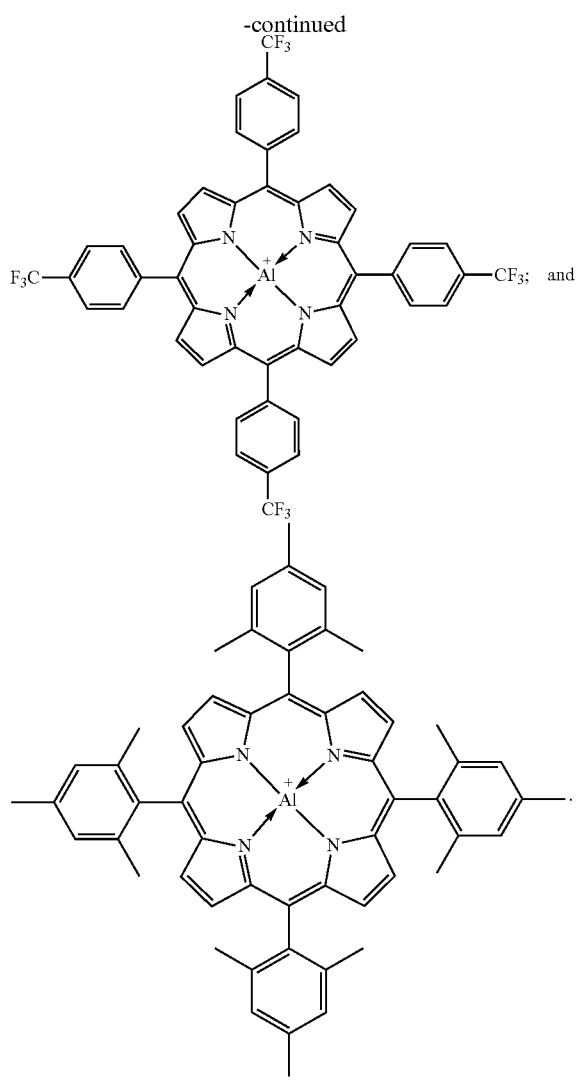

7. The method of claim 1, wherein the carbonylation catalyst is produced in a composition having a halide or alkali metal salt content in an amount less than about 200 ppm.

8. The method of claim 1, wherein $R^q$ is a $C_{1-12}$ alkyl group.

9. The method of claim 1, wherein $R^q$ is selected from the group consisting of methyl, ethyl, n-propyl, i-propyl, n-butyl, i-butyl, and octyl.

10. The method of claim 1, wherein $R^q$ is ethyl.

11. The method of claim 1, wherein the compound of formula I is:

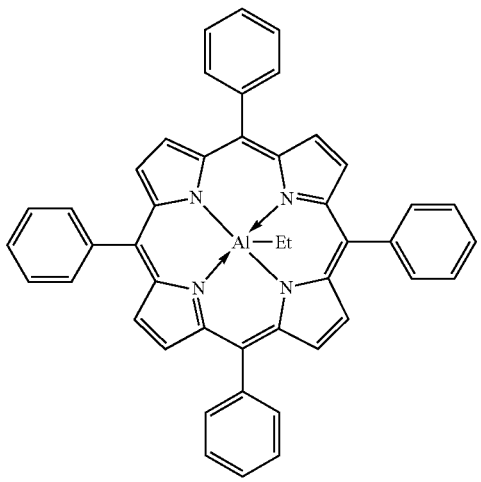

* * * * *